(12) United States Patent
Peters et al.

(10) Patent No.: US 12,009,061 B2
(45) Date of Patent: Jun. 11, 2024

(54) COMPUTATIONAL FILTERING OF METHYLATED SEQUENCE DATA FOR PREDICTIVE MODELING

(71) Applicant: University of Pittsburgh—Of the Commonwealth System of Higher Education, Pittsburgh, PA (US)

(72) Inventors: David Gerard Peters, Pittsburgh, PA (US); Tianjiao Chu, Pittsburgh, PA (US); Lisa Ann Pan, Pittsburgh, PA (US); David N. Finegold, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 455 days.

(21) Appl. No.: 16/846,238

(22) Filed: Apr. 10, 2020

(65) Prior Publication Data
US 2020/0327959 A1    Oct. 15, 2020

Related U.S. Application Data

(60) Provisional application No. 63/007,208, filed on Apr. 8, 2020, provisional application No. 63/007,218, filed
(Continued)

(51) Int. Cl.
*G16B 30/00* (2019.01)
*G16B 5/00* (2019.01)
(Continued)

(52) U.S. Cl.
CPC .............. *G16B 30/00* (2019.02); *G16B 5/00* (2019.02); *G16B 20/00* (2019.02); *G16B 40/20* (2019.02);
(Continued)

(58) Field of Classification Search
CPC ........ G16H 50/20; G16H 50/30; G16B 20/00; G16B 30/00; G16B 40/20; G16B 5/00
See application file for complete search history.

(56) References Cited

U.S. PATENT DOCUMENTS

| 5,427,930 A | 6/1995 | Birkenmeyer |
| 5,744,311 A | 4/1998 | Fraiser et al. |

(Continued)

FOREIGN PATENT DOCUMENTS

| EP | 0320308 | 6/1989 |
| WO | WO 1990/001069 | 2/1990 |

(Continued)

OTHER PUBLICATIONS

Goel, Neelam, Priya Karir, and Vivek Kumar Garg. "Role of DNA methylation in human age prediction." Mechanisms of ageing and development 166 (2017): 33-41.*

(Continued)

*Primary Examiner* — Steven W Crabb
*Assistant Examiner* — Nithya J. Moll
(74) *Attorney, Agent, or Firm* — Fish & Richardson P.C.

(57) ABSTRACT

Computational techniques are disclosed for using methylation profiles to classify the medication condition of a person. Initial sequence data is obtained containing sequences of an initial set of nucleic acids from a biological sample of a person. The initial sequence data is filtered to generate filtered sequence data that describes sequences of a filtered subset of nucleic acids from the biological sample. A methylation profile is determined for the filtered subset of nucleic acids from the biological sample. The methylation profile can be processed to determine a likelihood that the person has the specified medical condition. The system outputs an indication of the likelihood that the person has the specified medical condition.

31 Claims, 7 Drawing Sheets

Related U.S. Application Data on Apr. 8, 2020, provisional application No. 63/007,204, filed on Apr. 8, 2020, provisional application No. 62/928,156, filed on Oct. 30, 2019, provisional application No. 62/882,215, filed on Aug. 2, 2019, provisional application No. 62/832,157, filed on Apr. 10, 2019.

(51) Int. Cl.
| G16B 20/00 | (2019.01) |
|---|---|
| G16B 40/20 | (2019.01) |
| G16B 50/20 | (2019.01) |
| G16B 50/30 | (2019.01) |
| G16H 10/40 | (2018.01) |
| G16H 50/20 | (2018.01) |
| G16H 50/30 | (2018.01) |

(52) U.S. Cl.
CPC ............ *G16B 50/20* (2019.02); *G16B 50/30* (2019.02); *G16H 10/40* (2018.01); *G16H 50/20* (2018.01); *G16H 50/30* (2018.01)

(56) References Cited

U.S. PATENT DOCUMENTS

| 6,025,134 | A | 2/2000 | Sooknanan |
|---|---|---|---|
| 6,027,889 | A | 2/2000 | Barany et al. |
| 6,033,881 | A | 3/2000 | Himmler et al. |
| 8,067,168 | B2 | 11/2011 | Ordway et al. |
| 9,416,404 | B2 | 8/2016 | Sukumar et al. |
| 9,868,992 | B2 | 1/2018 | Goel et al. |
| 9,984,201 | B2 | 5/2018 | Zhang et al. |
| 10,329,621 | B2 | 6/2019 | Brock et al. |
| 10,612,086 | B2 | 4/2020 | Ehrich et al. |
| 10,683,555 | B2 | 6/2020 | Ahlquist et al. |
| 2005/0153440 | A1 | 7/2005 | Feinberg et al. |
| 2010/0105049 | A1 | 4/2010 | Ehrich et al. |
| 2012/0053071 | A1 | 3/2012 | Dimitrova et al. |
| 2013/0189684 | A1 | 7/2013 | Ehrich et al. |
| 2014/0031255 | A1 | 1/2014 | Rudi et al. |
| 2014/0162370 | A1 | 6/2014 | Ling et al. |
| 2015/0275304 | A1 | 10/2015 | Ehrich et al. |
| 2017/0175205 | A1 | 6/2017 | Toung et al. |
| 2018/0068083 | A1 | 3/2018 | Cohen et al. |
| 2018/0105884 | A1 | 4/2018 | Lo et al. |
| 2018/0305759 | A1 | 10/2018 | Micallef et al. |

FOREIGN PATENT DOCUMENTS

| WO | WO 2014/152985 | 9/2014 |
|---|---|---|
| WO | WO 2017/212428 | 12/2017 |
| WO | WO 2019/046725 | 3/2019 |

OTHER PUBLICATIONS

Zheng, Hao, et al. "CpGIMethPred: computational model for predicting methylation status of CpG islands in human genome." BMC medical genomics 6.1 (2013): 1-12.*

Previti, Christopher, et al. "Novel approaches to the prediction of CpG islands and their methylation status." Proceedings of the 2007 Summer Computer Simulation Conference. 2007.*

Abdolmaleky et al., "Hypomethylation of MB-COMT promoter is a major risk factor for schizophrenia and bipolar disorder," Hum. Mol. Genetics, Nov. 2006, 15(21):3132-3145.

Ahmad et al., "Expression of a SOX1 overlapping transcript in neural differentiation and cancer models," Cell Mol. Life Sciences, Jul. 2017, 74(22):4245-4258.

Akalin et al., "Methylkit: A comprehensive r package for the analysis of genome-wide DNA methylation profiles," Genome Biology, Oct. 2012, 13:R87, 9 pages.

Alberry, "Free fetal DNA in maternal plasma in anembryonic pregnancies: confirmation that the origin is the trophoblast," Prenatal Diagnosis, May 2007, 27(5):415-418.

Aljanabi et al., "Universal and rapid salt-extraction of high quality genomic DNA for PCR-based techniques," Nucleic Acids Research, Nov. 1997, 25(22):4692-4693.

Askvig et al., "Neuronal activity and axonal sprouting differentially regulate CNTF and CNTF receptor complex in the rat supraoptic nucleus," Exp. Neurology, Jan. 2012, 233(1):243-252.

Aydemir et al., "Fecal calprotectin levels are increased in infants with necrotizing enterocolitis," J. Matern. Fetal Neonatal Medicine, Nov. 2012, 25(11):2237-2241.

Ball et al., "Targeted and genome-scale strategies reveal gene-body methylation signatures in human cells," Nat. Biotechnology, Apr. 2009, 27(4):361-368.

Behnia et al., "Fetal DNA methylation of autism spectrum disorders candidate genes: Association with spontaneous preterm birth," Am. J. Obstet. Gynecology, Apr. 2015, 212(4):533.e1-533.e9.

Benadiba et al., "The Ciliogenic Transcription Factor RFX3 Regulates Early Midline Distribution of Guidepost Neurons Required for Corpus Callosum Development," PLoS Genetics, Mar. 2012, 8(3):e1002606, 16 pages.

Benjamini et al., "Controlling the False Discovery Rate: a Practical and Powerful Approach to Multiple Testing," J. R. Statist. Soc. B, Jan. 1995, 57(1):289-300.

Blair et al., "Widespread DNA Hypomethylation at Gene Enhancer Regions in Placentas Associated with Early-Onset Preeclampsia," Mol. Hum. Reproduction, Oct. 2013, 19(10):697-708.

BluestarGenomics,com [online], "Bluestar Genomics," available on or before Oct. 1, 2018, via Internet Archive: Wayback Machine URL<https://web.archive.org/web/20181001052644/https://www.bluestargenomics.com/>, retrieved on Jun. 7, 2021, retrieved from URL<https://www.bluestargenomics.com/#about>, 8 pages.

Boschi et al., "Differential Expression of Polycytosine-Binding Protein Isoforms in Adrenal Gland, Locus Coeruleus and Midbrain," Neuroscience, Feb. 2015, 286:1-12.

Buijck et al., "Sniffing Out Paediatric Gastro-intestinal Diseases: the Potential of Volatile Organic Compounds as Biomarkers for Disease," J. Pediatr. Gastroenterol. Nutrition, Dec. 2016, 63(6):585-591.

Bunce et al., "Discovery of epigenetic biomarkers for the noninvasive diagnosis of fetal disease," Prenatal Diagnosis, Jun. 2012, 32(6):542-549.

Burris et al., "Associations of line-1 DNA methylation with preterm birth in a prospective cohort study," J. Dev. Orig. Health Disease, Jun. 2012, 3(3):173-181.

Camunas-Soler et al., "Noninvasive Prenatal Diagnosis of Single-Gene Disorders by Use of Droplet Digital PCR," Clin. Chemistry, Feb. 2018, 64(2):336-345.

Catov et al., "Neonatal outcomes following preterm birth classified according to placental features." Am. J. Obstet. Gynecology, Apr. 2017, 216(4):411.e1-411.e14.

Catov et al., "Placental pathology measures: Can they be rapidly and reliably integrated into large-scale perinatal studies?" Placenta, Jun. 2015, 36(6):687-692.

Chaouat et al., "An insight into normal and pathological pregnancies using large-scale microarrays: lessons from microarrays," J. Reprod. Immunology, May 2011, 89(2):163-172.

Chen et al., "Methylation Alterations of the MyoD1 Upstream Region are Predictive of Subclassification of Human Rhabdomyosarcomas," Am. J. Pathology, Apr. 1998, 152(4):1071-1079.

Chia et al., "Phosphorylation of LRRK2 by casein kinase 1α regulates trans-Golgi clustering via differential interaction with ARHGEF7," Nat, Communications, Dec. 2014, 5:5827, 11 pages.

Chiu et al., "Noninvasive prenatal diagnosis of fetal chromosomal aneuploidy by massively parallel genomic sequencing of DNA in maternal plasma." Proc. Natl. Acad. Sci. USA, Dec. 2008, 105(51):20458-20463.

Cho et al., "Anoctamin 1 expression in the mouse auditory brainstem." Cell Tissue Research, Sep. 2014, 357(3):563-569.

(56) References Cited

OTHER PUBLICATIONS

Chu et al., "A microarray-based approach for the identification of epigenetic biomarkers for the noninvasive diagnosis of fetal disease," Prenatal Diagnosis, Nov. 2009, 29(11):1020-1030.

Chu et al., "Comparative evaluation of the Minimally-Invasive Karyotyping (MINK) algorithm for non-invasive prenatal testing," PLoS One, Mar. 2017, 12(3):e0171882, 14 pages.

Chu et al., "Comprehensive Analysis of Preeclampsia-Associated DNA Methylation in the Placenta," PLoS One, Sep. 2014, 9(9):e107318, 11 pages.

Chu et al., "High Levels of Sample-to-Sample Variation Confound Data Analysis for Non-Invasive Prenatal Screening of Fetal Microdeletions," PLoS One, Jun. 2016, 11(6):e0153182, 12 pages.

Chu et al., "High resolution non-invasive detection of a fetal microdeletion using the GCREM algorithm," Prenatal Diagnosis, May 2014, 34(5):469-477.

Chu et al., "Statistical model for whole genome sequencing and its application to minimally invasive diagnosis of fetal genetic disease," Bioinformatics, May 2009, 25(10):1244-1250.

Chu et al., "Structural and Regulatory Characterization of the Placental Epigenome at Its Maternal Interface," PLoS One, Feb. 2011, 6(2):e14723, 15 pages.

ClinicalTrials.gov [online], "Circulating Markers in Preterm Infants With Perinatal and Neonatal Inflammation (NEOINFLAM)," NCT03320785, Oct. 25, 2017, last updated Mar. 18, 2021, retrieved on May 4, 2021, retrieved from URL<https://clinicaltrials.gov/ct2/show/NCT03320785>, 13 pages.

ClinicalTrials.gov [online], "Use of Faecal Calprotectin to Predict Enteropathy of the Preterm Neonates (CALPROPREMA)," NCT02010268, Dec. 12, 2013, last updated Dec. 21, 2017, retrieved on May 4, 2021, retrieved from URL<https://clinicaltrials.gov/ct2/show/NCT02010268>, 12 pages.

Cologuard.com [online], "Cologuard," available on or before Aug. 5, 2011, via Internet Archive: Wayback Machine URL<https://web.archive.org/web/20110805130400/https://www.cologuard.com/>, retrieved on Jun. 7, 2021, retrieved from URL<https://www.cologuard.com/>, 3 pages.

De Mendoza et al., "A Systematic Review of DNA Methylation and Preterm Birth in African American Women," Biol. Res. Nursing, May 2017, 19(3):308-317.

De Rubis et al., "Liquid Biopsies in Cancer Diagnosis, Monitoring, and Prognosis," Trends Pharmacol. Sciences, Mar. 2019, 40(3):172-186.

DeRisi et al., "Use of a cDNA microarray to analyse gene expression patterns in human cancer," Nat. Genetics, Dec. 1996, 14(4):457-460.

DiNunzio et al., "CNS Disorders—Current Treatment Options and the Prospects for Advanced Therapies," Drug Dev. Ind. Pharmacy, Jan. 2008, 34(11):1141-1167.

DotLab.com [online], "DotLab," available on or before Jul. 8, 2017, via Internet Archive: Wayback Machine URL<https://web.archive.org/web/20170708230205/https://www.dotlab.com/>, retrieved on Jun. 7, 2021, retrieved from URL<https://www.dotlab.com/>, 4 pages.

EpiproColon.com [online], "Epi proColon," available on or before May 11, 2014, via Internet Archive: Wayback Machine URL<https://web.archive.org/web/20140511103429/https://www.epiprocolon.com/us/>, retrieved on Jun. 7, 2021, retrieved from URL<https://www.epiprocolon.com/us/>, 2 pages.

Fan et al., "Noninvasive diagnosis of fetal aneuploidy by shotgun sequencing DNA from maternal blood," Proc. Natl. Acad. Sci. USA, Oct. 2008, 105(42):16266-16271.

FoundationMedicine.com [online], "FoundationOne CDx," available on or before Jul. 20, 2020, via Internet Archive: Wayback Machine URL<https://web.archive.org/web/20200720091932/https://www.foundationmedicine.com/test/foundationone-cdx>, retrieved on Jun. 7, 2021, retrieved from URL<https://www.foundationmedicine.com/test/foundationone-cdx>, 9 pages.

Ghosh et al., "Liquid biopsy: A new avenue in pathology," Cytopathology, Mar. 2019, 30(2):138-143.

Grail.com [online], "Grail," available on or before Jan. 25, 2018, via Internet Archive: Wayback Machine URL<https://web.archive.org/web/20180125102931/https://grail.com/>, retrieved on Jun. 7, 2021, retrieved from URL<https://grail.com/>, 5 pages.

Grassi et al., "Neuronal Activity, TGFβ-Signaling and Unpredictable Chronic Stress Modulate Transcription of Gadd45 Family Members and DNA Methylation in the Hippocampus," Cereb. Cortex, Aug. 2017, 27(8):4166-4181.

GuardantHealth.com [online], "Solutions," available on or before Jul. 27, 2019, via Internet Archive: Wayback Machine URL<https://web.archive.org/web/20190727082849/https://guardanthealth.com/solutions/>, retrieved on Jun. 7, 2021, retrieved from URL<https://guardanthealth.com/solutions/>, 13 pages.

Gustincich et al., "A fast method for high-quality genomic DNA extraction from whole human blood." Biotechniques, Sep. 1991, 11(3):298-302.

Hammond et al., "Extraction of DNA from Preserved Animal Specimens for Use in Randomly Amplified Polymorphic DNA Analysis," Anal. Biochemistry, Sep. 1996, 240(2):298-300.

Han et al., "Variation of long-chain 3-hydroxyacyl-coa dehydrogenase DNA methylation in placenta of different preeclampsia-like mouse models," Chinese Journal of Obstetrics and Gynecology, Oct. 2015, 50(10):740-746 (with English Abstract).

Hardy et al., "Plasma DNA methylation: a potential biomarker for stratification of liver fibrosis in non-alcoholic fatty liver disease," Gut, Jul. 2017, 66(7):1321-1328.

Heng et al., "Maternal Whole Blood Gene Expression at 18 and 28 Weeks of Gestation Associated with Spontaneous Preterm Birth in Asymptomatic Women," PLoS One, Jun. 2016, 11(6):e0155191, 17 pages.

Hiemcke-Jiwa et al., "Molecular analysis in liquid biopsies for diagnostics of primary central nervous system lymphoma: review of literature and future opportunities," Crit. Rev. Oncol. Hematology, Jul. 2018, 127:56-65.

Hiemcke-Jiwa et al., "Potential Diagnosis of Vitreoretinal Lymphoma by Detection of MYD88 Mutation in Aqueous Humor with Ultrasensitive Droplet Digital Polymerase Chain Reaction," JAMA Ophthalmology, Oct. 2018, 136(10):1098-1104.

Hiemcke-Jiwa et al., "The use of droplet digital PCR in liquid biopsies: A highly sensitive technique for MYD88 p.(L265P) detection in cerebrospinal fluid," Hematol, Oncology, Dec. 6, 2017, 36(2):429-435.

Hong et al., "Genome-wide DNA methylation associations with spontaneous preterm birth in US blacks: findings in maternal and cord blood samples," Epigenetics, Feb. 2018, 13(2):163-172.

Huang et al., "Cell-Free DNA Methylation Profiling Analysis—Technologies and Bioinformatics," Cancers, Nov. 6, 2019, 11(11):1741, 22 pages.

Illingworth et al., "CpG islands—'A rough guide'," FEBS Letters, Jun. 2009, 583(11):1713-1720.

Illumina.com [online], "Getting started with NIPT," available on or before Oct. 28, 2020, via Internet Archive: Wayback Machine URL<https://web.archive.org/web/20201028153407/https://www.illumina.com/clinical/reproductive-genetic-health/nipt/healthcare-providers/getting-started.html>, retrieved on Jun. 7, 2021, retrieved from URL<https://www.illumina.com/clinical/reproductive-genetic-health/nipt/healthcare-providers/getting-started.html>, 2 pages.

Jiang et al., "Gestational Age Assessment by Methylation and Size Profiling of Maternal Plasma DNA: A Feasibility Study," Clin. Chemistry, Feb. 2017, 63(2):606-608.

Jiang et al., "NCS-Rapgef2, the Protein Product of the Neuronal Rapgef2 Gene, Is a Specific Activator of D1 Dopamine Receptor-Dependent ERK Phosphorylation in Mouse Brain," eNeuro, Sep. 2017, 4(5):e0248-17.2017, 17 pages.

Kang et al., "CancerLocator: non-invasive cancer diagnosis and tissue-of-origin prediction using methylation profiles of cell-free DNA," Genome Biology, Mar. 24, 2017, 18(1):53, 12 pages.

Kang et al., "Preeclampsia leads to dysregulation of various signaling pathways in placenta," J. Hypertension, May 2011, 29(5):928-936.

Karlas et al., "Correlation of cell-free DNA plasma concentration with severity of non-alcoholic fatty liver disease," J. Transl. Medicine, May 2017, 15(1):106, 9 pages.

(56) References Cited

OTHER PUBLICATIONS

Koh et al., "Noninvasive in vivo monitoring of tissue-specific global gene expression in humans," Proc. Natl. Acad. Sci. USA, May 2014, 111(20):7361-7366.
Krueger et al., "Bismark: a flexible aligner and methylation caller for Bisulfite-Seq applications," Bioinformatics, Jun. 2011, 27(11):1571-1572.
Lanoue et al., "The Wnt receptor Ryk is a negative regulator of mammalian dendrite morphogenesis." Sci. Reports, Jul. 2017, 7(1):5965, 11 pages.
Lapaire et al., "Microarray Screening for Novel Preeclampsia Biomarker Candidates," Fetal Diagn. Therapy, Mar. 2012, 31(3):147-153.
Lau et al., "Noninvasive prenatal testing for fetal chromosomal abnormalities by low-coverage whole-genome sequencing of maternal plasma DNA: Review of 1982 consecutive cases in a single center," Ultrasound Obstet. Gynecology, Mar. 2014, 43(3):254-264.
Liggett et al., "Methylation patterns of cell-free plasma DNA in relapsing-remitting multiple sclerosis," J. Neurol. Sciences., Mar. 2010, 290(1-2):16-21.
Liu et al., "DNA methylation at imprint regulatory regions in preterm birth and infection," Am. J. Obstet. Gynecology, May 2013, 208(5):395.e1-395.e7.
Liu et al., "β-Arrestin-biased signaling mediates memory reconsolidation.," Proc. Natl. Acad. Sci. USA, Apr. 2015, 112(14):4483-4488.
Lo et al., "Digital PCR for the molecular detection of fetal chromosomal aneuploidy," Proc. Natl. Acad. Sci. USA, Aug. 2007, 104(32):13116-13121.
Lo et al., "Fetal DNA in Maternal Plasma/Serum: The First 5 Years," Pediatr. Research, Jan. 2003, 53(1):16-17.
Lopez et al., "A molecular multi-gene classifier for disease diagnostics," Nat. Chemistry, Apr. 30, 2018, 10:746-754.
Lumellapoc.com [online], "Lumella," available on or before Nov. 3, 2016, via Internet Archive: Wayback Machine URL<https://web.archive.org/web/20161103101359/https://lumellapoc.com/>; retrieved on Jun. 7, 2021, retrieved from URL<https://lumellapoc.com/>, 6 pages.
Lun et al., "Microfluidics Digital PCR Reveals a Higher than Expected Fraction of Fetal DNA in Maternal Plasma," Clin. Chemistry, Oct. 2008, 54(10):1664-1672.
Mayne et al., "Accelerated placental aging in early onset preeclampsia pregnancies identified by DNA methylation," Epigenomics, Mar. 2017, 9(3):279-289.
Menon et al., "DNA Methylation: An Epigenetic Risk Factor in Preterm Birth," Reprod. Sciences, Jan. 2012, 19(1):6-13.
Muinelo-Romay et al., "Liquid Biopsy in Endometrial Cancer: New Opportunities for Personalized Oncology," Int. J. Mol. Sciences, Aug. 2018, 19(8):2311, 12 pages.
Nakayuenyongsuk et al., "Point-of-Care Fecal Calprotectin Monitoring in Preterm Infants at Risk for Necrotizing Enterocolitis," J. Pediatrics, May 1, 2018, 196:98-103.e1.
Natera.com [online], "Natera," available on or before Feb. 3, 2017, via Internet Archive: Wayback Machine URL<https://web.archive.org/web/20170203203636/https://www.natera.com/>, retrieved on Jun. 7, 2021, retrieved from URL<https://www.natera.com/>, 4 pages.
Ng et al., "Comparative MIRNA Expressional Profiles and Molecular Networks in Human Small Bowel Tissues of Necrotizing Enterocolitis and Spontaneous Intestinal Perforation," PLoS One, Aug. 14, 2015, 10(8):0135737, 17 pages.
Ng et al., "Gut-associated biomarkers L-FABP, I-FABP, and TFF3 and LIT score for diagnosis of surgical necrotizing enterocolitis in preterm infants," Ann. Surgery, Dec. 2013, 258(6):1111-1118.
Ngo et al., "Noninvasive blood tests for fetal development predict gestational age and preterm delivery," Science, Jun. 2018, 360(6393):1133-1136.
Ohtsuka et al., "Gene Expression Profiling of Neural Stem Cells and Identification of Regulators of Neural Differentiation During Cortical Development," Stem Cells, Nov. 2011, 29(11):1817-1828.
OncotypeIQ.com [online], "OncotypeIQ," available on or before May 15, 2017, via Internet Archive: Wayback Machine URL<https://web.archive.org/web/20170515010901/https://www.oncotypeiq.com/en-US>, retrieved on Jun. 7, 2021, retrieved from URL<https://www.oncotypeiq.com/en-US>, 5 pages.
Pandya et al., "Correlation profiling of brain sub-cellular proteomes reveals co-assembly of synaptic proteins and subcellular distribution," Sci. Reports, Sep. 2017, 7(1):12107, 11 pages.
Parets et al., "DNA methylation provides insight into intergenerational risk for preterm birth in African Americans." Epigenetics, Sep. 2015, 10(9):784-792.
Parets et al., "Fetal DNA Methylation Associates with Early Spontaneous Preterm Birth and Gestational Age," PLoS One, Jun. 2013, 8(6):e67489, 8 pages.
Park et al., "Differential methylation analysis for BS-seq data under general experimental design," Bioinformatics, May 2016, 32(10):1446-1453.
Park et al., "MethylSig: a whole genome DNA methylation analysis pipeline," Bioinformatics, Sep. 2014, 30(17):2414-2422.
PCT International Search Report and Written Opinion in International Appln. No. PCT/US2020/027839, dated Jul. 16, 2020, 11 pages.
Peters et al., "Noninvasive Prenatal Diagnosis of a Fetal Microdeletion Syndrome," N. Engl. J. Medicine, Nov. 2011, 365:1847-1848.
Qiu et al., "Essential Role of PDZ-RGS3 in the Maintenance of Neural Progenitor Cells," Stem Cells, Sep. 2010, 28(9):1602-1610.
Qiu et al., "Regulation of neural progenitor cell state by ephrin-B," J. Cell Biology, Jun. 2008, 181(6):973-983.
Rabinowitz et al., "Noninvasive Aneuploidy Detection by Multiplexed Amplification and Sequencing of Polymorphic Loci," Obstet. Gynecology, May 2014, 123(Suppl. 1):167S.
Ramaswamy et al., "Multiclass cancer diagnosis using tumor gene expression signatures," Proc. Natl. Acad. Sci. USA, Dec. 2001, 98(26):15149-15154.
Roche.com [online], "cobas® EGFR Mutation Text v2," available on or before May 10, 2020, via Internet Archive: Wayback Machine URL:https://web.archive.org/web/20200510165123/https://diagnostics.roche.com/us/en/products/params/cobas-egfr-mutation-test-v2.html, retrieved on Jun. 7, 2021, retrieved from URL:https://diagnostics.roche.com/us/en/products/params/cobas-egfr-mutation-test-v2.html>, 6 pages.
Sadri et al., "Rapid analysis of DNA methylation using new restriction enzyme sites created by bisulfite modification," Nucleic Acids Research, Dec. 1996, 24(24):5058-5059.
Sanchez-Mora et al., "Case—Control Genome-Wide Association Study of Persistent Attention-Deficit Hyperactivity Disorder Identifies FBXO33 as a Novel Susceptibility Gene for the Disorder." Neuropsychopharmacology, Mar. 2015, 40(4):915-926.
Santoro et al., "BAG3 is involved in neuronal differentiation and migration." Cell Tissue Research, Feb. 2017, 368(2):249-258.
Seoane et al., "The European Society for Medical Oncology (ESMO) Precision Medicine Glossary," Ann. Oncology, Jan. 2018, 29(1):30-35.
Shen et al., "Sensitive tumour detection and classification using plasma cell-free DNA methylomes," Nature, Nov. 2018, 563(7732):579-583.
Song et al., "5-Hydroxymethylcytosine signatures in cell-free DNA provide information about tumor types and stages," Cell Research, Aug. 18, 2017, 27(10):1231-1242.
StageZeroLifeSciences.com [online], "Aristotle™," available on or before Nov. 1, 2019, via Internet Archive: Wayback Machine URL<https://web.archive.org/web/20191101231409/https://www.stagezerolifesciences.com/aristotle.html>, retrieved on Jun. 7, 2021, retrieved from URL<https://www.stagezerolifesciences.com/aristotle.html>, s5 pages.
Strauss et al., "Spontaneous Preterm Birth: Advances Toward the Discovery of Genetic Predisposition," Am. J. Obstet. Gynecology, Mar. 2018, 218(3):294-314.e2.
Stricker et al., "Functions of the neuron-specific protein ADAP1 (centaurin-α1) in neuronal differentiation and neurodegenerative diseases, with an overview of structural and biochemical properties of ADAP1," Biol. Chemistry, Nov. 2014, 395(11):1321-1340.

(56) References Cited

OTHER PUBLICATIONS

Sun et al., "Noninvasive reconstruction of placental methylome from maternal plasma DNA: Potential for prenatal testing and monitoring," Prenatal Diagnosis, Feb. 2018, 38(3):196-203.

Sunnucks et al., "Microsatellite and Chromosome Evolution of Parthenogenetic Sitobion Aphids in Australia." Genetics, Oct. 1996, 144(2):747-756.

Takai et al., "Comprehensive analysis of CpG islands in human chromosomes 21 and 22." Proc. Natl. Acad. Sci. USA, Mar. 2002, 99(6):3740-3745.

Teo et al., "Cell-free DNA as a biomarker of aging," Aging Cell, Feb. 2019, 18(1):e12890, 14 pages.

Ulz et al., "Inferring expressed genes by whole-genome sequencing of plasma DNA," Nat. Genetics, Aug. 2016, 48(10):1273-1278.

Van den Berg et al., "Early- and late-onset preeclampsia and the DNA methylation of circadian clock and clock-controlled genes in placental and newborn tissues," Chronobiol. International, Aug. 2017, 34(7):921-932.

Van Vliet et al., "Epigenetic mechanisms in the context of complex diseases," Cell. Mol. Life Sciences, Jun. 2007, 64(12):1531-1538.

Varkonyi et al., "Microarray Profiling Reveals That Placental Transcriptomes of Early-Onset HELLP Syndrome and Preeclampsia Are Similar," Placenta, Feb. 2011, 32(0):S21-S29.

Vidal et al., "Maternal Stress, Preterm Birth, and DNA Methylation at Imprint Regulatory Sequences in Humans," Genet, Epigenetics, Jan. 2014, 6(6):37-44.

Wang et al., "Comparison of DNA methylation profiles associated with spontaneous preterm birth in placenta and cord blood," BMC Med. Genomics, Dec. 2019, 12:1, 14 pages.

Wang et al., "Using classification models for the generation of disease-specific medications from biomedical literature and clinical data repository," J Biomed. Informatics, May 2017, 69:259-266.

Winn et al., "The Impact of Preeclampsia on Gene Expression at the Maternal-Fetal Interface." Pregnancy Hypertension, Jan. 2011, 1(1):100-108.

Xiong et al., "COBRA: a sensitive and quantitative DNA methylation assay," Nucleic Acids Research, Jun. 1997, 25(12):2532-2534.

Xuan et al., "Comprehensive analysis of DNA methylation and gene expression of placental tissue in preeclampsia patients," Hypertens. Pregnancy, Jan. 2016, 35(1):129-138.

Yamada et al., "A Comprehensive Analysis of Allelic Methylation Status of CpG Islands on Human Chromosome 21q," Genome Research, Feb. 2004, 14(2):247-266.

Yatsenko et al., "Maternal cell-free DNA-based screening for fetal microdeletion and the importance of careful diagnostic follow-up." Genet. Medicine, Oct. 2015, 17(10):836-838.

Ye et al., "Bisphenol a exposure alters placentation and causes preeclampsia-like features in pregnant mice involved in reprogramming of DNA methylation of WNT2," Faseb Journal, Feb. 2019, 33(2):2732-2742.

Ye et al., "Cdk5-mediated phosphorylation of RapGEF2 controls neuronal migration in the developing cerebral cortex," Nat. Communications, Sep. 2014, 5:4826, 14 pages.

Yeung et al., "DNA methylation profiles in preeclampsia and healthy control placentas," Am. J. Physiol. Heart Circ. Physiology, May 2016, 310(10):H1295-1303.

Yong et al., "Profiling genome-wide DNA methylation," Epigenetics Chromatin, Jun. 2016, 9:26, 16 pages.

Yu et al., "Size-based molecular diagnostics using plasma DNA for noninvasive prenatal testing." Proc. Natl. Acad. Sci. USA, Jun. 2014, 111(23):8583-8588.

Yuen et al., "DNA methylation profiling of human placentas reveals promoter hypomethylation of multiple genes in early-onset preeclampsia." Eur. J. Hum, Genetics, Sep. 2010, 18(9):1006-1012.

Zhang et al., "Altered DNA methylation and transcription of wnt2 and dkk1 genes in placentas associated with early-onset preeclampsia," Clin. Chim. Acta., Mar. 2019, 490:154-160.

Zhang et al., "Predicting genome-wide DNA methylation using methylation marks, genomic position, and DNA regulatory elements," Genome Biology, Dec. 2015, 16(1):14, 20 pages.

Zhou et al., "KLF15 regulates dopamine D2 receptor and participates in mouse models of neuropathic pain," Biochem. Biophys. Res. Communications, Oct. 2017, 492(2):269-274.

PCT International Preliminary Report on Patentability in International Appln. No. PCT/US2020/027839, dated Sep. 28, 2021, 10 pages.

U.S. Appl. No. 17/602,553, filed Oct. 8, 2021, David Gerard Peters.

\* cited by examiner

COMPUTATIONAL FILTERING OF METHYLATED SEQUENCE DATA FOR PREDICTIVE MODELING

CROSS-REFERENCE TO RELATED APPLICATIONS

This application claims the benefit of priority to U.S. application Ser. No. 62/832,157, filed on Apr. 10, 2019, U.S. application Ser. No. 62/882,215, filed on Aug. 2, 2019, U.S. application Ser. No. 62/928,156, filed on Oct. 30, 2019, U.S. application Ser. No. 63/007,204, filed on Apr. 8, 2020, U.S. application Ser. No. 63/007,208 filed on Apr. 8, 2020, and U.S. application Ser. No. 63/007,218, filed on Apr. 8, 2020. The disclosures of each of these applications are considered part of the disclosure of the present document, and are each incorporated by reference in their entireties.

GOVERNMENT FUNDING STATEMENT

This invention was made with government support under grant number HD068578 awarded by the National Institutes of Health. The government has certain rights in the invention.

BACKGROUND

1. Technical Field

This document relates to systems and methods for classifying a condition of a mammal (e.g., a human) using predictive models (e.g., machine-learning models) that process methylation patterns of DNA obtained from a biological sample. Certain implementations of the techniques described herein employ computational methods to perform filtering operations on an input data set that can improve efficiency of the prediction or classification task while increasing model sensitivity.

2. Background Information

Machine-learning involves the analysis of data samples to identify features and patterns in the data samples that can be employed to perform tasks such as classification and prediction without explicit instructions. Some machine-learning techniques determine a model for performing the desired task, such as a neural network, a regression model, a decision tree, a support vector machine, and a naive Bayes machine.

Methylation patterns in a mammal's DNA have been correlated with certain medical conditions or phenotypes of the mammal. However, data sets describing DNA sequences and/or methylation patterns are typically quite large and can be computationally expensive to process.

SUMMARY

This document describes systems, methods, devices, and other techniques for training and applying models to classify a medical condition of a person or other mammal based on methylation patterns occurring in DNA sequences of the person. In some aspects, the disclosed techniques employ a filtering operation to enrich a subset of sequences represented in an initial data set based on methylation characteristics and/or copy number characteristics of the nucleic acids. The filtering operation can, in some embodiments, achieve advantages including reducing the size of the input data set (e.g., a methylation profile) provided to the classifier (e.g., a machine-learning model), decreasing the time and computational expense required to process the input data set, and/or improving the sensitivity of the model to patterns that have the highest predictive power in differentiating persons with normal from abnormal medical conditions.

In some aspects, the disclosed techniques can involve identifying a set of reference CpG sites of abnormal individuals. Computing systems can estimate either restricted reference component methylomes or mixture methylomes that are independent linear combinations of certain reference component methylomes. The proportions of these components at the reference CpG sites for the tested biological samples can further be estimated, and the system can then predict the methylation level of the tested biological samples at a target set of CpG sites under the hypothesis that the sample is from a normal individual. The predicted methylation levels can then be compared against the observed methylation levels, and a classification for the individual as either exhibiting a normal or abnormal condition with respect to the specified medical condition can then be determined.

Further implementations of the disclosed subject matter include methods performed by a computing system. The system can obtain initial sequence data that describes sequences of an initial set of nucleic acids from a biological sample of a person, the initial set of nucleic acids including nucleic acids originating from multiple different tissues of the person. The system can filter the initial sequence data to generate filtered sequence data that describes sequences of a filtered subset of nucleic acids from the biological sample. Filtering can include (i) selecting target nucleic acids from the initial set of nucleic acids based on at least one of a methylation characteristic or a copy number characteristic of the target nucleic acids and (ii) enriching the target nucleic acids in the filtered subset. A methylation profile can be determined for the filtered subset of nucleic acids from the biological sample. The system processes the methylation profile for the filtered subset of nucleic acids to determine a likelihood that the person has a specified medical condition, and an indication of the likelihood that the person has the specified medical condition can then be provided as an output of the system.

These and other implementations can further include one or more of the following features.

The system can identify a pre-defined set of genomic regions (i.e., genomic loci). Selecting target nucleic acids from the initial set of nucleic acids can include comparing nucleic acid sequences from the initial set of nucleic acids to sequences from the pre-defined set of genomic regions. Enriching the target nucleic acids in the filtered subset can include discarding nucleic acid sequences from the initial sequence data that are not among the sequences from the pre-defined set of genomic regions, while retaining nucleic acid sequences from the initial sequence data that are among the sequences from the pre-defined set of genomic regions. At least a first subset of the pre-defined set of genomic regions can be defined based on those regions in the first subset exhibiting a minimum level of stability with respect to at least one of the methylation characteristic or the copy number characteristic in a population of individuals.

The biological sample can be plasma, and the initial set of nucleic acids can include cell-free DNA in the plasma.

The method can further include actions of identifying a set of restricted reference component methylomes in the initial set or filtered subset of nucleic acids; identifying a set of reference component methylomes; determining a proportion of the reference component methylomes at a reference set of CpG sites in the initial set or filtered subset of nucleic acids; generating predictions of methylation levels at a target set of CpG sites in the initial set or filtered subset of nucleic acids; comparing the predictions of methylation levels at the target set of CpG sites to observed methylation levels; and determining whether the person likely has or does not have the specified medical condition based on the comparison.

The biological sample can be a stool sample.

The biological sample can be cerebrospinal fluid.

The initial set of nucleic acids can be treated to facilitate detection of methylated sites before sequencing.

The specified medical condition can be ovarian cancer, endometriosis, necrotizing enterocolitis, fetal aneuploidy, preeclampsia, or a brain condition.

The methylation profile for the filtered subset of nucleic acids can indicate, for each of a set of multiple genomic loci, a methylation level of the locus. The genomic loci can be a CpG site, CpG island, differentially methylated region (DMR), promoter region, enhancer region, or CpG island shore.

Determining the likelihood that the person has the specified medical condition can include determining a probability that the person has the specified medical condition.

Determining the likelihood that the person has the specified medical condition can include generating a binary indication that the person either likely has the specified medical condition or likely does not have the specified medical condition.

Processing the methylation profile can include providing data representing the methylation profile as input to a machine-learning model, and obtaining the likelihood, or a value from which the likelihood is derived, as an output of the machine-learning model.

The machine-learning model can include at least one of a classifier, an artificial neural network, a support vector machine, a decision tree, or a regression model.

The machine-learning model can define reference or predicted methylation profiles against which the methylation profile for the filtered subset are compared to determine the likelihood that the person has the specified medical condition.

The determined likelihood that the person has the specified medical condition can be used by a medical provider to assess whether to perform additional diagnostic testing on the person.

The determined likelihood that the person has the specified medical condition can be used by a medical provider to at least one of diagnose the person or treat the person for the specified medical condition.

Outputting the indication of the likelihood that the person has the specified medical condition can include at least one of presenting the indication on an electronic display, audibly playing the indication through a speaker, storing the indication in a memory of a computing system for subsequent retrieval, or transmitting the indication in an electronic message to one or more users.

Enriching the target nucleic acids in the filtered subset can include generating the filtered subset so that a fraction of the target nucleic acids that occur in the filtered subset is greater than a fraction of the target nucleic acids that occur in the initial set of nucleic acids.

The filtered subset can consist exclusively of the target nucleic acids. Alternatively, the filtered subset can include both the target nucleic acids and non-targeted nucleic acids.

Some implementations include yet another method performed by a computing system. The method can include actions of obtaining initial sequence data that describes sequences of an initial set of nucleic acids from a biological sample of a person, the initial set of nucleic acids including nucleic acids originating from a multiple different tissues of the person; filtering, by the computing system, the initial sequence data to identify a first subset of sequences from the initial sequence data that correspond to a first pre-defined set of genomic regions; filtering, by the computing system, the initial sequence data to identify a second subset of sequences from the initial sequence data that correspond to a second pre-defined set of genomic regions; processing, by the computing system, data that includes an observed methylation profile of the first subset of sequences to generate a predicted methylation profile of the second subset of sequences; comparing, by the computing system, an observed methylation profile of the second subset of sequences to the predicted methylation profile of the second subset of sequences to determine whether the person has a specified medical condition, wherein the person is deemed to have the specified medical condition if a difference between the observed methylation profile of the second subset of sequences and the predicted methylation profile of the second subset of sequences meets a minimum difference criterion; and outputting, by the computing system, an indication of whether the person was determined to have the specified medical condition.

These and other implementations can further include one or more of the following features.

The first pre-defined set of genomic regions can be regions that exhibit a minimum level of stability with respect to at least one of a methylation characteristic or a copy number characteristic in a population of individuals. The second pre-defined set of genomic regions can be regions that exhibit a minimum difference with respect to at least one of the methylation characteristic or the copy number characteristic between a first sub-population of individuals who have the specified medical condition and a second sub-population of individuals who do not have the specified medical condition.

The first pre-defined set of genomic regions can be a first reference set of genomic regions, and the second pre-defined set of genomic regions can be a first target set of genomic regions. The actions can further include selecting the first reference set of genomic regions as the first pre-defined set of genomic regions from a database that includes multiple reference sets of genomic regions, wherein different ones of the multile reference sets of genomic regions correspond to different medical conditions; and selecting the first target set of genomic regions as the second pre-defined set of genomic regions from the database, wherein the database further includes a multiple target sets of genomic regions, wherein different ones of the multiple target sets of genomic regions correspond to different medical conditions.

The specified medical condition is preeclampsia, endometriosis, ovarian cancer, necrotizing enterocolitis, or a brain condition.

Some implementations include yet another method performed by a computing system. The method can include actions of obtaining, by a computing system, initial sequence data that describes sequences of an initial set of nucleic acids from a biological sample of a person, the initial set of nucleic acids including nucleic acids originating from multiple different tissues of the person; filtering, by the computing system, the initial sequence data to identify a target subset of sequences from the initial sequence data that correspond to a pre-defined set of genomic regions; comparing, by the computing system, an observed methylation profile of the target subset of sequences to a pre-defined methylation profile to determine whether the person has a specified medical condition, wherein the person is deemed to have the specified medical condition if a difference between the observed methylation profile of the target subset of sequences and the pre-defined methylation profile meets a minimum difference criterion; and outputting, by the computing system, an indication of whether the person was determined to have the specified medical condition.

Additional aspects of the disclosed subject matter includes a computing system having one or more processors and one or more computer-readable media having instructions stored thereon that, when executed by the one or more processors, cause the one or more processors to perform actions of any of the methods/processes disclosed herein. Further aspects include one or more computer-readable media having instructions stored thereon that, when executed by one or more processors, cause the one or more processors to perform actions of any of the methods/processes disclosed herein.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

Other features and advantages of the invention will be apparent from the following detailed description, and from the claims.

DETAILED DESCRIPTION

Figure 1:
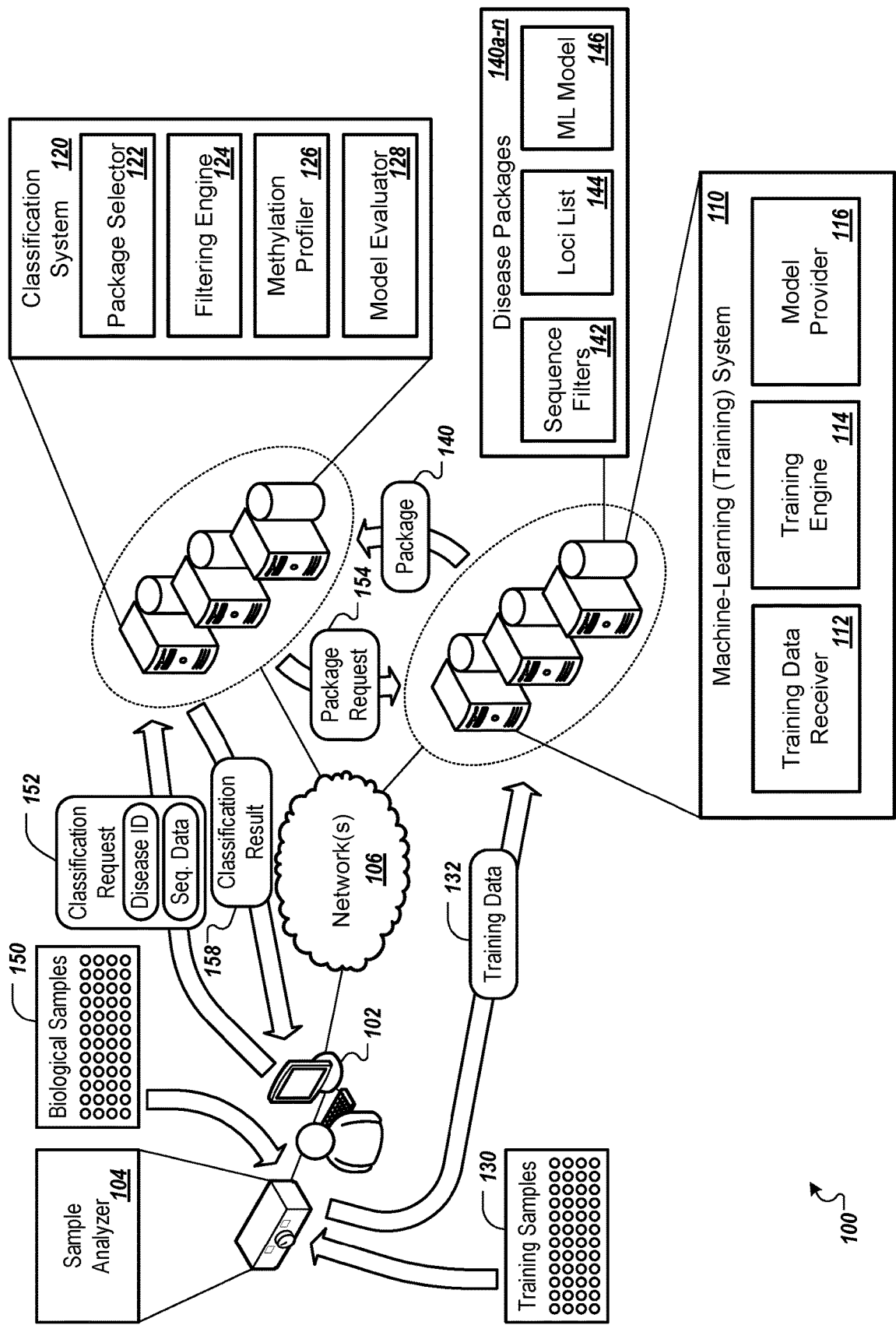
FIG. 1 depicts a computing environment adapted for processing of sequence data to classify a patient as likely or not likely exhibiting a specified medical condition.

FIG. 1 depicts a computing environment 100 adapted for processing of sequence data to classify a patient as likely or not likely exhibiting a specified medical condition. The environment 100 is configured to train machine-learning model(s) corresponding to one or more medical conditions, and to apply the trained machine-learning models in classification tasks that facilitate screening, diagnosis, and/or treatment of medical conditions of a patient. In some examples, the computing environment 100 allows for improved efficiency and accuracy in screening for conditions such as pre-eclampsia, ovarian cancer, endometriosis, necrotizing enterocolitis, fetal aneuploidy, and/or certain brain or nervous system disorders, through analysis of sequence data derived from biological samples obtained from a patient via minimally invasive techniques (e.g., plasma or stool samples). The computing environment 100 can further employ filtering engines that filter an initial batch of sequencing data to reduce the universe of nucleic acids analyzed when classifying a given medical condition, thereby improving sensitivity of the classifier, while reducing model size and reducing the number of operations required to generate a classification result.

Environment 100 includes a sample analyzer 104 that processes and sequences biological samples 150 from a person. In some implementations, the system is configured to perform "liquid biopsies" on liquid-based biological samples 150 from a person, e.g., plasma samples, stool samples, saliva samples, cerebrospinal fluid samples, urine samples, or cervical swab samples. The plasma (or other biological samples) may include cell-free DNA from the person (and, in some cases, cell-free DNA from a fetus if the person is a pregnant female). Cell-free DNA can originate from various tissues in a person's body. For example, cell-free DNA in a biological sample 150 can include fragments of DNA that were released from cells as a result of processes such as active secretion, necrosis, apoptosis, or a combination of these. The level of cell-free DNA in a sample 150 originating from certain tissue(s) can be correlated with a given medical condition (e.g., disease). Moreover, the methylation patterns of cell-free DNA originating from certain tissue(s), and which occur in the biological sample 150, can be correlated with a medical condition (e.g., disease) of the person. To analyze the level of cell-free DNA or other nucleic acids associated with a specified medical condition, and to analyze the methylation patterns of these nucleic acids, the sample analyzer 104 may process the biological sample 150 to generate initial sequence data for the fragments of extracellular DNA and/or other nucleic acids in the sample 150.

The initial sequence data describes sequences of nucleotides occurring in nucleic acids from the sample 150, e.g., sequences of bases along fragments of cell-free DNA. Typically, the initial sequence data includes sequence descriptions for both targeted nucleic acids and background (non-targeted) nucleic acids in the biological sample 150. The targeted nucleic acids are those that are deemed significant to detection of a specified medical condition, while the background nucleic acids are deemed insignificant or less significant to detection of the specified medical condition. The mixture of targeted and background nucleic acids may vary for different medical conditions. For example, some nucleic acids may be classified in the target set for detection of ovarian cancer, while those same acids may be classified in the background set for detection of necrotizing enterocolitis. In some implementations, the set of target nucleic acids that are deemed significant to a particular medical condition are those originating from particular tissue(s) affected by a specified medical condition. For instance, the target nucleic acids associated with endometriosis may include or consist of cell-free DNA from the endometrium or uterus. Likewise, the target nucleic acids associated with necrotizing enterocolitis may be based on intestinal tissue. Often, the fraction of targeted nucleic acids in the biological sample is small in relation to the fraction of background nucleic acids, and the fraction of sequences reflected in the initial sequence data for targeted nucleic acids may also be small in relation to sequences of background nucleic acids. As a result, the initial sequence data may contain substantial levels of "noise" relative to the signals present in the sequences for targeted nucleic acids, which can degrade the performance of models in predicting whether or not a patient likely has a specified medical condition.

The sample analyzer 104 is configured to sequence nucleic acids in the biological sample 150 using any suitable technique, including polymerase chain reaction (PCR)-based methods such as droplet digital PCR, or next-generation sequencing (NGS). In some implementations, nucleic acids from the biological sample 150 undergo bisulfite conversion before sequencing in order to facilitate subsequent detection of methylated sites. Bisfulite treatment has the effect of converting unmethylated cytosines (C) to uracil (U), which in turn are converted to thymine (T) in the course of DNA amplification. In contrast, bisulfite treatment does not affect methylated cytosines (C). As a result, bisulfite conversion enables differentiation of methylated from non-methylated cytosines, which appear as different bases in the sequencing data. Methylation arrays, methylation-specific PCR, enrichment, and/or additional methods may also or alternatively be applied.

Sample analyzer 104 can output initial sequencing data for a biological sample 150 for receipt by a user's computing system 102. The user's computing system 102 can comprise one or more computers in one or more locations. System 102 can be, for example, a desktop computer, notebook computer, tablet computer, or smartphone. System 102 includes a network interface for communicating over one or more networks 106 such as a local area network (LAN), a wireless LAN (WLAN), the Internet, or a combination of these. System 102 may include peripherals such as a keyboard, pointing device, and display screen to enable user interaction with the system 102. In some implementations, the user may coordinate activities at the system 102 for obtaining a classification result related to a specified medical condition based on sequencing data from biological sample 150. For example, upon obtaining initial sequencing data from sample analyzer 104, the user may instruct system 102 to send a classification request 152 to classification system 120. Classification system 120 can comprise one or more computers in one or more locations. System 120 may be located remotely from the user's system 102, or may be located at the same premises on system 102. In some implementations, the capabilities of systems 102, 120, 110, or any two of these, are consolidated in a single, integrated system. In general, classification system 120 processes a classification request 152 and returns a classification result 158 that indicates a predicted likelihood that the person who provided biological sample 150 either has or does not have a specified medical condition (e.g., preeclampsia, necrotizing enterocolitis, endometriosis, ovarian cancer, fetal aneuploidy, an abnormal brain condition, or others).

In more detail, classification system 120 can include a package selector 122, filtering engine 124, methylation profiler 126, and model evaluator 128. Each of these components 122, 124, 126, and 128 may be implemented on one or more computers using a combination of software, hardware, or firmware. Package selector 122 is operable to select, from a library of medical-condition packages 140a-n, a particular package 140 that corresponds to the medical condition specified in classification request 152. Each package 140a-n defines information or instructions usable by classification system 120 to generate a classification result as to a different medical condition. In some implementations, the package 140 for a given medical condition can include one or more sequence filters 142, a loci list 144, and a machine-learning (ML) model 146, each of which is specific to the corresponding medical condition. Classification system 120 can load a retrieved package 140 to facilitate generation of a classification result 158 responsive to request 152. In some implementations, package selector 122 can select individual components of a package 140 as needed, such as filters 142, loci list 144, or ML model 146, to the exclusion of the others.

Sequence filters 142 provide information that enable a filtering engine 124 of the classification system 120 to filter initial sequence data by retaining sequences for target nucleic acids corresponding to the specified medical condition and discarding sequences for background (non-targeted) nucleic acids for the specified medical condition. In some implementations, filters 142 provides a whitelist that identifies target nucleic acids that should be retained in a filtering operation, such as cell-free DNA fragments that originate uniquely from a particular tissue associated with the specified medical condition. In some implementations, filters 142 provide a blacklist that identifies background nucleic acids that should be discarded in a filtering operation, such as cell-free DNA fragments that are not uniquely originated from a particular tissue associated with the specified medical conditions. In some implementations, filters 142 provide a whitelist that identifies target nucleic acids that should be retained (while other nucleic acids not specified in the whitelist are discarded) in a filtering operation, such as cell-free DNA fragments that are uniquely originated from a particular tissue associated with the specified medical condition. The whitelist, blacklist, or other information in filters 142 can define a set of genomic regions or sequences of nucleic acids against which sequences in the initial set of nucleic acids from the classification request 152 are compared to assess whether to retain or discard for further processing. For example, all nucleic acids in a plasma sample can be sequenced and the filtering can remove certain sequences identified in the blacklist. Alternatively, all nucleic acids in the sample can be sequenced and the filtering can discard everything but the sequences identified in a whitelist.

In some implementations, the filtering engine 124 is configured to perform a filtering operation that involves (i) selecting target nucleic acids from the initial set of nucleic acids based a methylation characteristic (e.g., methylation status), a copy number characteristic of the target nucleic acids, or both, and (ii) enriching the target nucleic acids, e.g., to increase a fraction of the target nucleic acids after filtering relative to their fraction in a pre-filtered set. In some examples, filters 142 identify a set of genomic regions in a whitelist. Selecting target nucleic acids from the initial set of nucleic acids can include comparing sequences of nucleic acids from the initial set of nucleic acids to sequences in the pre-defined set of genomic regions. Enriching the target nucleic acids in the filtered subset can include discarding sequences of nucleic acids from the initial set of nucleic acids that do not appear in the pre-defined set of regions, while retaining nucleic acids that do appear in the pre-defined set of regions. The pre-defined set of genomic regions can identify target nucleic acids having at least a minimum level of stability (e.g., minimum threshold stability) with respect to the methylation characteristic and the copy number characteristic, wherein the identified target nucleic acids originate from multiple different tissues. Additionally or alternatively, the pre-defined set of genomic regions can identify target nucleic acids originating from a subset of the multiple different tissues for which at least one of the methylation characteristic or the copy number characteristic differs by at least a minimum amount (e.g., minimum threshold) between individuals who have the specified medical condition and individuals who do not have the specified medical condition. In other examples, filters 142 identify a pre-defined set of genomic regions or sequences in a blacklist/exclude list, and corresponding operations can apply to select and enrich target nucleic acids except that the target nucleic acids are identified by discarding nucleic acids within the blacklist/exclude list.

Loci list 144 identifies the set of genomic loci whose methylation statuses are processed to generate a classification result with respect to a particular medical condition. The methylation profiler 126 within classification system 120 can use the loci list 144 to construct a methylation profile for a set of nucleic acids. For example, the loci list 144 may identify specific nucleotides, CpG sites, CpG islands, differentially methylated regions, promoter regions, enhancer regions, and/or CPG island shores whose methylation statuses can be processed to inform a classification with respect to the corresponding medical condition. In some implementations, the loci list 144 identifies genomic loci that occur only within the set of target nucleic acids for the medical condition. The loci list 144 can provide that the methylation statuses of all CpG sites within the target nucleic acids should be processed to generate a classification result. Alternatively, the loci list 144 can provide that the methylation statuses of only a subset of CpG sites within the target nucleic acids should be processed to generate a classification result. The subset of CpG sites (or other genomic loci) can be deemed the most statistically significant, or those that have the highest predictive power, for accurately classifying whether a patient has or does not have a specified medical condition. In some implementations, the loci list 144 identifies genomic loci that occur anywhere in the genome, regardless of whether the loci occur in target or background nucleic acid. The genomic loci in this embodiment may be processed without a separate filtering step that discards all or some of the background nucleic acid sequences, and the loci may have been identified as the most statistically significant, or those having the highest predictive power across the genome for accurately classifying whether a patient has or does not have a specified medical condition. The methylation profiler 126 can analyze the initial set of sequence data from the classification request 152 or the filtered set of sequence data from filtering engine 124 to determine the methylation status of all or some of the loci identified in list 144. The methylation status can be expressed in a number of ways, such as a binary value indicating whether the methylation level at a locus is above or below a pre-defined threshold, or a normalized value within a pre-defined range of values indicating a relative methylation level at the locus across multiple DNA fragments encompassing the locus.

As used interchangeably herein, "methylation state," "methylation profile," "methylation status," and "methylation level" refer to the presence, absence, percentage, and/or quantity of methylation at a particular nucleotide, or nucleotides, within a DNA region, e.g., a genomic locus. The methylation status of a particular DNA sequence (e.g., a genomic locus) can indicate the methylation state of every nucleotide in the sequence, indicate the methylation state of any of the nucleotides (e.g., cytosines) in the sequence, can indicate the methylation state of a subset of the nucleotides (e.g., of cytosines), can indicate the percentage or fraction of methylated cytosines at any particular stretch of nucleotides within the sequence or can indicate the average rate of methylation of all the cytosines (or a subset of the cytosines) present in a nucleic acid.

As used herein, a "methylated nucleic acid molecule" refers to a nucleic acid molecule that contains one or more methylated nucleotides that is/are methylated.

As used herein, a "CpG site" or "methylation site" is a nucleotide within a nucleic acid that is susceptible to methylation either by natural occurring events in vivo or by an event instituted to chemically methylate the nucleotide in vitro. A "CpG island," as used herein, describes a segment of a nucleic acid, e.g., DNA sequence, that have a high frequency of CpG dinucleotide repeats. A "CpG island shore," as used herein, refers to methylation hotspots that are present a short distance, e.g., less than 2 kb, from CpG islands.

Machine-learning model 146 is a model that correlates methylation patterns from a methylation profile to likelihoods that a person has or does not have a specified medical condition. The machine-learning model 146 can be loaded by model evaluator 128 in classification system 120. Further details on training and applying machine-learning models are described with respect to FIGS. 5-7. For example, model evaluator 128 can provide the methylation profile from methylation profiler 126 as input to the machine-learning model 146, and can evaluate the machine-learning model 146 based on the methylation profile to generate a classification result 158 indicating whether the patient likely has or does not have the specified medical condition. The machine-learning model 146 can be implemented in a number of different forms. Typically, model 146 is trained using supervised learning techniques, and can be a linear regression model, logistic regression model, decision tree, support vector machine, naive bayes model, random forest model, or artificial neural network (e.g., a feedforward neural network, deep neural network, recurrent neural network, and/or convolutional neural network), or a combination of two or more of these.

Environment 100 can further include a machine-learning system 110 for training the machine-learning models 146 in the library of packages 140 *a-n*. System 110 can be implemented one or more computers in one or more locations, and may be accessible to the user's system 102 and classification system 120 via a direct connection or by connection over a network 106. In some implementations, the functionality of system 110 can be integrated with the user's system 102, classification system 120, or both. System 110 can include a training data receiver 112, training engine 114, and model provider 116. Receiver 112 is configured to receive training data 132 for training a machine-learning model. Different training data sets 132 can be used to train different models corresponding to different medical conditions. For example, a first training data set may be constructed for training a model that screens for pre-eclampsia, while a second training data set may be constructed for training a model that screens for endometriosis. The training data 132 can include a collection of training samples 130, each training sample 130 comprising (i) a set of filtered or unfiltered sequence data describing sequences of nucleic acids from a biological sample of a person and (ii) a label indicating whether or not the patient exhibits a specified medical condition. The label can serve as a target output for the model 146 when evaluated on a methylation profile derived from the sequence data in the training sample. Further details of a process for training a machine-learning model 146 is described below with respect to FIGS. 5 and 6. Training engine 114 receives the training data 132 from receiver 112 and processes this data 132 to train model 146. Trained model 116 can then be returned by model provider 116 and stored in a library in the package for the corresponding medical condition on which the model 116 was trained.

Figure 2:
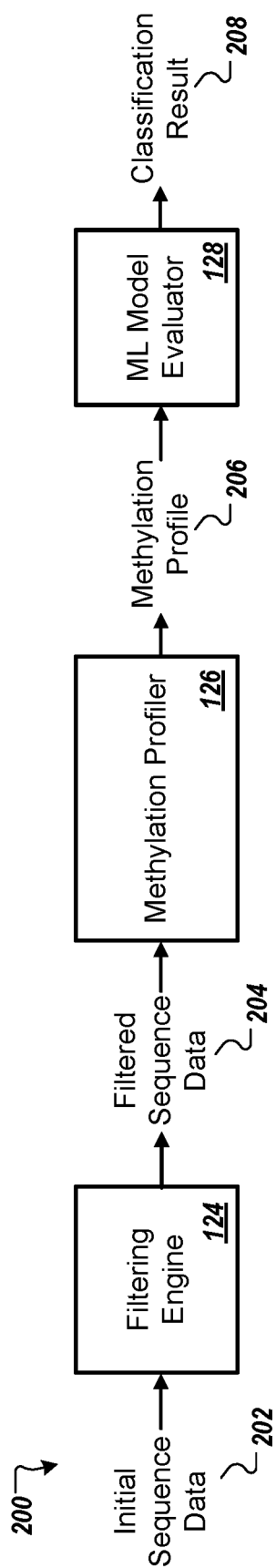
FIG. 2 is a functional illustration of a process for classifying a person as either exhibiting a specified medical condition or not based on methylation patterns in nucleic acids recovered from biological samples.

FIG. 2 depicts a functional illustration of a process 200 for classifying a person as either exhibiting a specified medical condition or not based on methylation patterns in nucleic acids recovered from biological samples such as plasma, cerebrospinal fluid, or stool. Filtering engine 124 receives initial sequence data 124, which contains information describing sequences of nucleic acids (e.g., cell-free DNA) from the biological sample. The initial sequence data 124 may include a relatively low fraction of sequences for target nucleic acids related to the specified medical condition and a relatively high fraction of sequences for background nucleic acids that are substantially unrelated to the medical condition. Filtering engine 124 performs a filtering operation on the initial sequence data 202 to generate filtered sequence data 204. Filtered sequence data 204 virtually enriches target nucleic acids in the specimen by discarding sequence data for all or some of the background nucleic acids. As a result, filtered sequence data 204 may include a higher fraction of sequences for the target nucleic acids than the fraction of the same sequences in initial sequence data 202. In some implementations, it is unnecessary for the filtering operation to completely distill the cohort of sequences to just those sequences for target nucleic acids. While complete distillation may be achieved in some cases, for many applications it is sufficient for the filtering operation to increase the fraction of sequences for the target nucleic acids relative to the fraction of sequences for the background nucleic to a threshold level such that the data is usable to generate a classification result with a minimally specified confidence level. Methylation profiler 126 then processes the filtered sequence data 204 to generate a methylation profile 206 that identifies a methylation status (e.g., methylation level) at each locus of a set of genomic loci within the target nucleic acids, or within a combination of target and background nucleic acids, represented in filtered sequence data 204. Machine-learning model evaluator 128 then uses a trained machine-learning model to process methylation profile 206 and generate a classification result 208 indicating the system's prediction as to whether the patient exhibits the specified medical condition.

Figure 3:
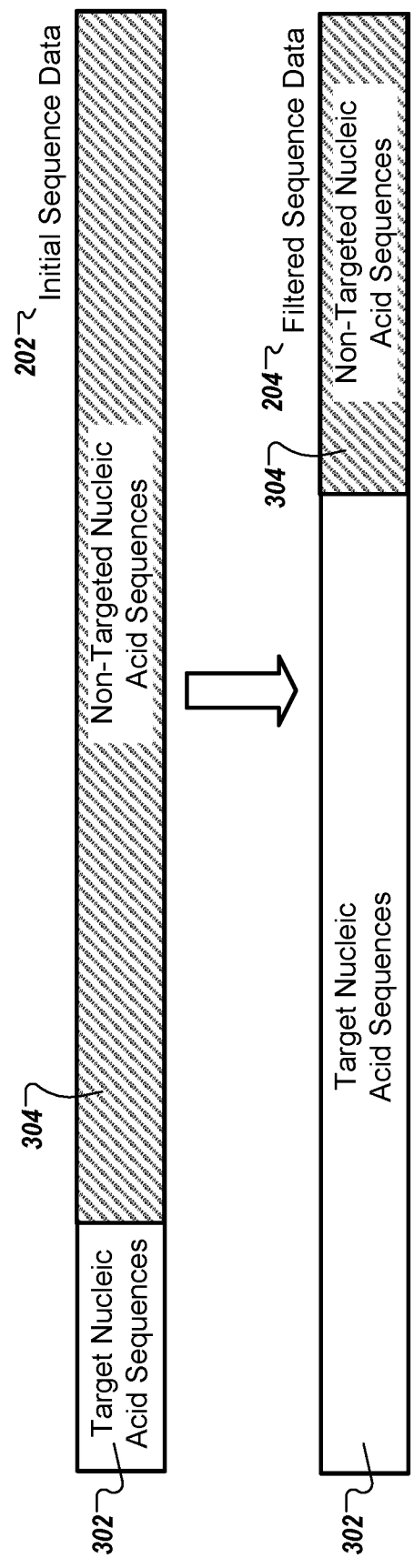
FIG. 3 is a depiction of a filtering operation that results in increasing the fraction of sequences for target nucleic acids in a set of sequence data.

Referring to FIG. 3, an illustration is shown of a filtering operation that results in increasing the fraction of sequences for target nucleic acids in a set of sequence data. The top bar in FIG. 3 represents a collection of initial sequence data, e.g., initial sequence data 202. The initial sequence data 202 includes a relatively small fraction 302 of target nucleic acid sequences and a relatively high fraction 304 of background (non-targeted) nucleic acid sequences. Due to the overwhelming presence of sequences for background nucleic acids in the initial data set 202, the significance of the sequences having greater predictive power for the target nucleic acids is diminished. After the filtering operation, however, a filtered sequence data set 204 results in a significantly higher fraction of target sequences 302 than occurs in the initial data set 202, and a lower fraction of non-target sequences 304.

Figure 4:
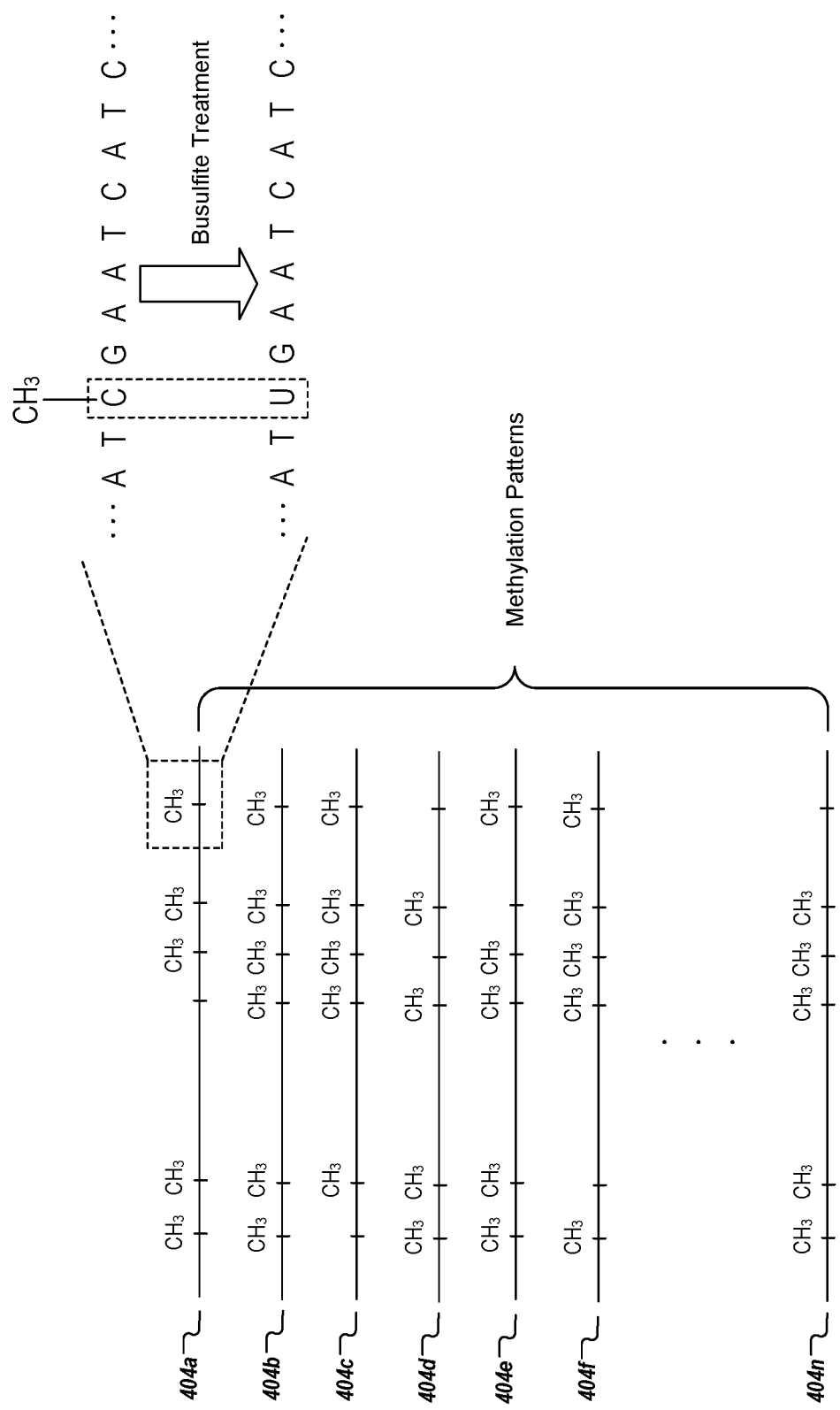
FIG. 4 illustrates a set of methylation patterns on multiple fragments of cell-free DNA of an individual, along with an example of a bisulfite treatment process.

FIG. 4 depicts a representation of a set of methylation patterns 404a-n on multiple fragments of cell-free DNA of an individual. Methyl groups ($CH_3$) bonded to the DNA at certain CpG sites form a methylation pattern on each fragment. In some implementations, methylation sites are detected by first treating the DNA with bisulfite to convert methylated cytosines to uracil, and interpreting the uracil sites as methylated sites in the original DNA strand. Other techniques for detecting methylated loci in nucleic acids may also be employed rather than or in addition to bisulfite conversion, although FIG. 4 illustrates a suitable method.

Figure 5:
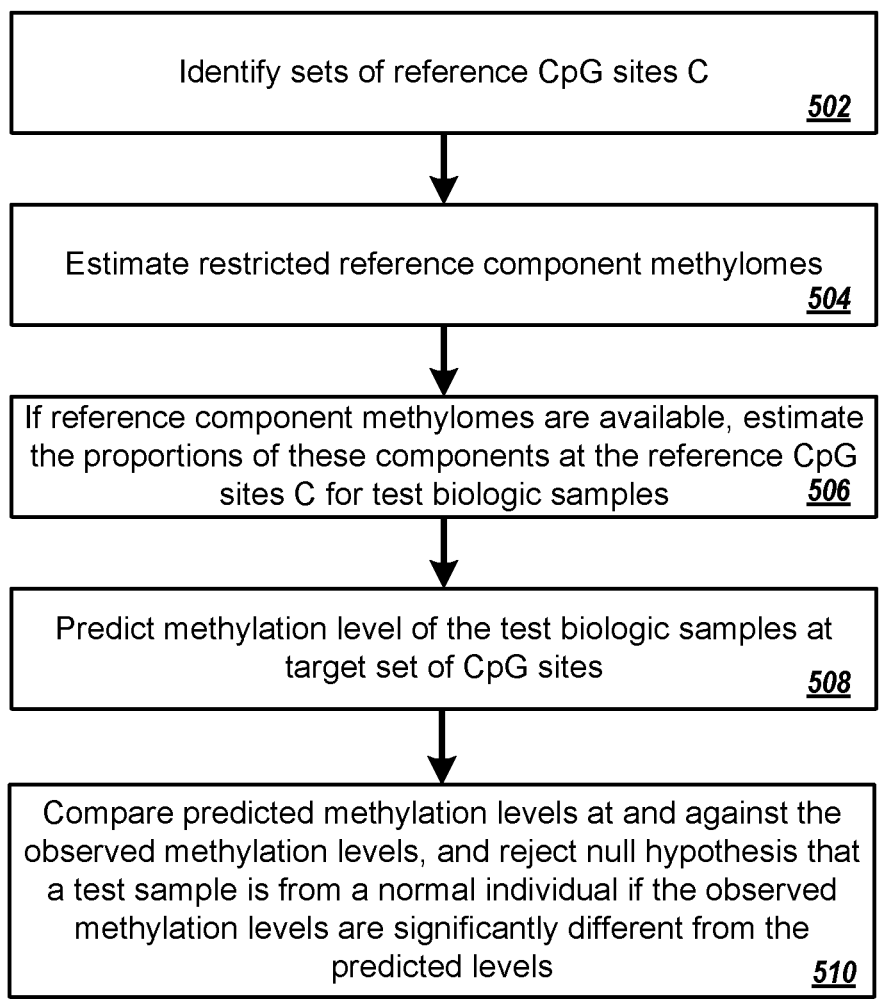
FIG. 5 is a flowchart of an example process for training and using a machine-learning model to determine whether a specified medical condition of a person or other mammal is or is not normal.

In some implementations, the systems and methods disclosed herein can be applied to generate a classification result indicating whether a patient likely does or does not have a specified medical condition according to the process 500 depicted in FIG. 5. The process 500 is based on the observation that the methylome(s) of certain tissue(s) in a person or other mammal can be affected by certain medical conditions that reflect diseases or abnormalities in the body (e.g., preeclampsia, endometriosis, necrotizing enterocolitis, or other conditions described herein), and that the changes of these methylomes can lead to changes in the methylation patterns of the DNA fragments found in a biological sample (e.g., a plasma, stool, urine, or saliva sample), which are released by these tissue(s). The term "methylome," as used herein, refers to the amount or pattern of methylation at different sites or regions within a population of cells. The methylome can correspond to all of the genome, a subset of the genome (e.g., repeat elements in the genome), or a portion of the subset (e.g., those areas found to be associated with a specified medical condition). A methylome from plasma can be referred to a "plasma fluid methylome" or a "plasma fluid DNA methylome." The plasma fluid methylome is an example of a cell-free methylome that includes cell-free DNA (cfDNA). A methylome from stool can be referred to a "stool fluid methylome" or a "stool fluid DNA methylome." The stool fluid methylome is an example of a cell-free methylome that includes cell-free DNA (cfDNA).

The process 500 was developed to identify changes of methylation patterns in the methylome of a biological sample caused by phenotypes of certain tissues affected by the abnormal medical condition (e.g., intestinal tissue for necrotizing enterocolitis or uterine tissue for endometriosis). One insight behind this process 500 was that the methylome of the DNA fragments in these biological samples is a mixture of a variety of component methylomes, and that the proportion of these different component methylomes in the mixture varies from subject to subject, even among the population with normal tissue phenotype. By constructing a model methylome for a biological sample as a linear combination of various component methylomes, the process 500 can accurately predict the methylation patterns of a new biological sample under the hypothesis that it is from a normal individual. Consequently, the process 500 can exhibit high sensitivity in detecting abnormal methylation patterns in a biological sample caused by changes of the methylomes of some tissues (e.g., intestinal tissues) when the sample is from an affected individual. The process 500 can be performed by any of the computing systems described herein, such as systems 102, 110, and 120 shown in the environment of FIG. 1.

Let i be any CpG site in human genome, $z_{i,j}$ be the methylation level of CpG site i in a biological sample j, $p_{i,r,j}$ be the proportion of the $r^{th}$ component methylome $m_{r,j}$ of particular tissue origin in sample j at site i, $m_{r,j}$ be the methylation level of CpG i in methylome $m_{r,j}$. The system models the scenario as follows:

$$z_{i,j} = \Sigma_{r=1}^{R} p_{i,r,j} m_{i,r,j} \qquad (1)$$

where $p_{i,r,j}, m_{i,r,j} >= 0, m_{i,r,j} <= 1, p_{i,1,j} + \cdots + p_{i,R,j} = 1$.

The model assumes that there is a set of CpG sites S such that, for any CpG site i in S, and any biological sample of a particular type (e.g., plasma, stool, cerebrospinal fluid, saliva, or urine) j from a normal individual, it has $m_{i,r,j}=m_{i,r}$ and $p_{i,r,j}=p_{r,j}$.

That is, the model assumes that in any biological sample from a normal individual, the proportions of different component methylomes in the mixture are the same for all CpG sites in S. The model further assumes that by restricting to the set of CpG sites S, biological samples from all normal individuals have the same set of component methylomes. They are called restricted reference component methylomes (RRCM), and are labeled as $m_1^S, \ldots, m_R^S$ or simply $m_1, \ldots, m_R$ when there is no confusion. For any biological sample j from a normal individual, its methylome restricted to set of CpG sites in S can be expressed as a weighted average of the restricted reference component methylomes. More precisely, let $z_j^S$ be the methylome of biological sample C restricted to S, then for some mixture vector $p_j=[p_{j,1}, \ldots, p_{j,R}]^T$, it has:

$$z_j^S = [m_1^S, \ldots, m_R^S] p_j \quad (2)$$

The model also assumes that the set S is the union of two disjoint subsets C and T, where T is a union of K non-empty sets $T_k$ such that $T=U_{k=1}^K T_k$ where the index k represents the $k^{th}$ type of abnormal tissue (e.g., intestinal tissue) phenotype. $T_k$'s do not need to be disjoint. Moreover, $T_k$ itself is the union of two disjoint sets $D_k$ and $V_k$. Either $D_k$ or $V_k$ could be empty, but not both. It is assumed that for any biological sample, including one from an abnormal individual, when restricted to CpG sites in C, its methylome can always be expressed as a weighted average of the restricted reference component methylomes. That is, it has: $z_j^C = [m_1^C, \ldots, m_R^C] p_j$ regardless whether j is from an abnormal individual. C is called the set of reference CpG sites. On the other hand, for a biologic sample 1 from an abnormal individual, when restricted to CpG sites in S=CUT, its methylome can no longer be expressed as a weighted average of the restricted reference component methylomes. That is, it has: $w_1^S \neq [m_1^S, \ldots, m_R^S] p_{1}$ for any mixture vector $p_1$. More specifically, for a biologic sample 1 from the $k^{th}$ type of abnormal individual, it has: 1) $w_j^C=[m_1^C, \ldots, m_R^C] p_l$, 2) if $D_K$ is non-empty, then $w_1^{D_k}=[m_{1,k}^{D_k}, \ldots, m_{R,k}^{D_k}] p_l$ such that $[m_1^{D_k}, \ldots, m_R^{D_k}] \neq [m_{1,k}^{D_k}, \ldots, m_{R,k}^{D_k}]$, and 3) if $V_k$ is non-empty, then $w_1^{V_k}=[m_1^{V_k}, \ldots, m_R^{V_k}] q_l$ such that $p_l \neq q_l$. In other words, in a biologic sample from the $k^{th}$ type of abnormal individual, if the set $D_k$ is not empty, the component methylomes of the sample l restricted to $D_k$ are no longer the same as the reference component methylome restricted to $D_k$. If the set $V_k$ is not empty, in this biologic sample, the proportion of the reference component methylomes restricted to $V_k$ is no longer the same as the proportion of the reference component methylome restricted to R.

T is called the target set of CpG sites, $D_k$ is called the differential methylation target set, $V_k$ is called the copy number variation target set, and $T_k$ is called the target set for the $k^{th}$ type of abnormal individual.

Certain operations of the process 500 are depicted in the flowchart of FIG. 5, which may be carried out by a system of one or more computers (e.g., systems 102, 110, and/or 120). First, the system identifies the sets of reference CpG sites C, and $T_1, \ldots, T_K$ for the list of K types of abnormal individuals (502). The system then estimates the restricted reference component methylomes $m_1, \ldots, m_R$, or R predictor methylomes $n_1, \ldots, n_R$ that are independent linear combinations of the reference component methylomes such that $n_r=[m_1, \ldots, m_R] q_r$, for R linearly independent mixture vectors $q_1, \ldots, q_R$ (504). If the reference component methylomes are available, the system estimates the proportions of these components at the reference CpG sites C for the test biologic samples (506). The system predicts the methylation level of the test biologic samples at the target set $T_k$ of CpG sites, under the hypothesis that the sample is from a normal individual (508). Then, the predicted methylation levels at $D_k$ and $V_k$ are compared against the observed methylation levels, and the system rejects the null hypothesis that a test sample is from a normal individual if the observed methylation levels are significantly different from the predicted levels (510). In this manner, a classification result can be generated indicating whether the person or other mammal from whom the biologic sample was obtained either has the specified medical condition (abnormal) or does not have the specified medical condition (normal).

Process 500 of FIG. 5 can be implemented in a number of ways. For example, given the methyl-sequence data for a set of biologic samples from normal individuals, an expectation-maximization (EM) technique or data augmentation technique can be applied to estimate the component methylomes, and then the maximum likelihood method used to estimate the proportion of these component methylomes in the test sample. Below are certain implementations that employ linear regression.

In some implementations of the presently disclosed process 500, it is assumed the restricted methylome of a biologic sample from a normal individual can be approximated by a mixture of two restricted reference methylomes, one representing the DNA fragments from a first specific tissue region (e.g., intestinal tissue region for necrotizing enterocolitis), another representing the DNA fragments from a second specific tissue region. It is further assumed that the estimations of these two reference component methylomes are available. The implementation of the process 500 includes the following steps.

To begin, identify the reference set C, and the target sets $T_1, \ldots, T_K$ (502). First, collect the methylation data for a set of first cell type samples, a set of second cell type samples, and a set of biologic samples, all from normal individuals. For each type of abnormal individuals, collect a set of first cell type samples, a set of second cell type samples, and a set of biologic samples from that type of abnormal individuals. All these samples should have matched age, race, and other relevant parameters. These are the training data. Next, let $x_{i,j}$ be the observed methylation level of CpG site i in a normal first cell type sample j, and $y_{i,1}$ the observed methylation level of CpG site i in a normal second cell type sample 1, $s_{x,i}^2$ the sample variance of $x_{i,j}$ over all normal first cell type samples, $s_{y,i}^2$ the sample variance of $y_{i,j}$ over all normal second cell type samples. Identify the CpG sites $S_0$ such that for any $i \in S_0$, it has both $s_{x,i}^2 < c_0$ and $s_{y,i,j}^2 < c_0$ for some constant $c_0$. These are CpG sites with stable methylation levels in each type of normal cells. Next, let $x_{i,j}$ be the observed methylation level of CpG site i in a first cell type sample j, including normal and abnormal, and $y_{i,1}$ the observed methylation level of CpG site i in a second cell type sample 1, including normal and abnormal, $s_{x,i}^2$ the sample variance of $x_{i,j}$ over all first cell type samples, including normal and abnormal, $s_{y,i}^2$ the sample variance of $y_{i,j}$ over all second cell type samples, including normal and abnormal. Identify the CpG sites $S_1$ such that for any $i \in S_1$, it has both $s_{x,i}^2 < c_0$ and $s_{y,i}^2 < c_0$ for some constant $c_0$, and that the statistical test for the difference between $\{x_{i,j0}: j0$ is a normal first cell type sample$\}$, and $\{x_{ijk}: jk$ is a first cell type sample of the kth abnormal phenotype$\}$, is not significant for all abnormal phenotypes of first cell type, and that the statistical test for the difference between $\{y_{i,j0}: j0$ is a normal second cell type sample} and $\{y_{i,j,k}$:jk is a second cell type sample of the kth abnormal phenotype} is not significant for all abnormal phenotypes of the second cell type. These are CpG sites with stable methylation levels in each type of cells, and with no difference in methylation level between normal and any abnormal samples. Let $x_i$ be the sample mean of $x_{i,j}$ over all first cell type samples, including normal and abnormal, $y_i$ the sample mean of $y_{i,j}$ over all second cell type samples, including normal and abnormal. Identify the subset $C_0$ of $S_1$ such that for any $i \in C_0$, it has $|x_i-y_i|>c_i$ for some constant $c_1$. These are CpG sites that are stably methylated in each cell type, with no difference between the normal and abnormal samples of the same cell type, and differentially methylated between different types of cells. Next, let $x^{R_0}$ be the vector of $x_i$ for all $i \in C_0$, and $y^{c_0}$ be the vector of $y_i$ for all $i \in C_0$, where $x_i$ is the mean methylation at site i in all first cell type samples $y_i$ the mean methylation at site i in all second cell type samples. Note that by the way the set $C_0$ is selected, there is no difference in the methylation level of any CpG sites in $C_0$ between normal and abnormal first cell type samples, or between normal and abnormal second cell type samples. Let $z_j^{c_0}$ be the observed methylation levels of CpG sites in $C_0$ for a biologic sample j of the $k^{th}$ abnormal type. (For convenience, the normal biologic sample is called as sample of the $0^{th}$ abnormal type). For each sample j belonging to the $k^{th}$ abnormal type, regress $z_j^{c_0}$ against $x^{c_0}$ and $y^{c_0}$, with the constraints that the intercept must be 0, and the coefficients must be non-negative and add to 1, and get the residual $e_j^{c_0}$. Identify the subset $C_o^k$ of $C_0$ such that for any CpG i in $C_0^k$, it has $$\frac{e_{i,k}^2}{s_{i,k}} < c_2, \text{ and } e_{i,k}^2 < c_3$$

for some constants $c_2$ and $c_3$, where $e_{i,k}^2$ is the mean of the squared difference between estimated and observed methylation levels of CpG site i in all biologic samples of the $k^{th}$ abnormal type, and $s_{i,k}^2$ the sample variances of methylation levels of CpG site i in the same set of biologic samples. Repeat the above procedure for each type of abnormal biologic samples, the intersection of the subsets $C=\cap_{k=0}^{k} C_0^k$ is the reference set of CpG sites. These are CpG sites where their methylation levels in both normal and any type of abnormal biologic samples can be accurately predicted by the reference component methylomes from normal individuals.

Next, let $T_0=S_0 \backslash S_1$. Let $x^c$ and $x^{T_0}$ be the vectors of $x_i$ and $x_h$ for all $i \in C$ and $h \in T_0$ respectively, and $y^c$ and $y^{T_0}$ be the vectors of $y_i$ and $y_h$ for all $i \in C$ and $h \in T_0$ respectively, where $x_i$, $x_h$, $y_i$, and $y_h$ are mean methylation level of sites for a normal first cell type sample or second cell type sample at sites i and h respectively. Let $z_j^C$ and $z_j^{T_0}$ and be the observed methylation levels of CpG sites in C and $T_0$ respectively for a normal biologic sample j, $w_{l_k}^c$ and $w_{l_k}^{T_0}$ the observed methylation level of CpG sites in C and $T_0$ respectively for a biologic sample $l_k$ from an individual with the $k^{th}$ type of abnormality, $w_{l_g}^c$ and $w_{l_g}^{T_0}$ the observed methylation level of CpG sites in C and $T_0$ respectively for a biologic sample $l_g$ from an individual with the $g^{th}$ type of abnormality, where $g \ne k$. For each j, $l_k$, and $l_g$, regress $z_j^c$, $w_{l_k}^c$ and $w_{l_g}^c$ respectively against $x^c$ and $y^c$, with the constraints that the intercept must be 0, and the coefficients must be non-negative and add to 1. Apply the fitted models respectively to $x^{T_0}$ and $y^{T_0}$ to predict $z_j^{T_0}$, $w_{l_k}^{T_0}$, and $w_{l_g}^{T_0}$ respectively, and get the differences $e_j^{T_0}$, $e_{l_k}^{T_0}$, and $e_{l_g}^{T_0}$ between the predicted values and observed values. Let $e_i$, $e_{i,k}$, and $e_{i,g}$ be the means of the sets of differences $\{e_j^{T_0}$:j is a normal biologic sample}, $\{e_{l_k}^{T_0}$:$l_k$ is a biologic sample of the $k^{th}$ abnormal type} and $\{e_{l_g}^{T_0}$:$l_g$ is a biologic sample of the $g^{th}$ abnormal type} for CpG site i respectively. Identify the subset $T_k$ of $T_0$ such that for any $i \in T_k$, it has $|e_i|<c_{2,0}$ $|e_{i,k}|>c_{s,k}$, and $|e_{i,k}-e_{i,g}|>c_{3,k}$, for some constants $c_{2,0}$, $c_{2,k}$, and $c_{3,k}$, for all $g \ne k$. $T_k$ is the target set for the $k^{th}$ type of the abnormal individual. These are the sites where the methylation of a normal biologic sample can be accurately predicted, the observed methylation in a biologic sample of the $k^{th}$ abnormal type will deviate from the prediction, and deviation will be different from that of a biologic sample of any other abnormal type Next, the system estimates the fraction of the new biologic samples to be tested. Recall that $x^c$ and $y^c$ are mean vectors of the methylation levels of the training first cell type and training second cell type data for the CpG sites in the reference set C. For any new biologic sample t to be tested, let $z_t^C$ be the observed methylation levels of CpG sites in C. Regress $z_t^C$ against $x^C$ and $y^C$, with the constraints that the intercept must be 0, and the coefficients must be non-negative and add to 1. The estimated coefficients for $x^C$ are the estimated fractions of the two cell types for the biologic sample t.

The system can then test if the new biologic samples are from the $k^{th}$ type of abnormal individual. For the new biologic sample (e.g., plasma) t, let $x^{T_k}$ and $y^{T_k}$ be mean vectors of the methylation levels of the training the first cell type data and the second cell type data for the CpG sites in the target set $T_k$ identified in step 1 of this process 500, apply the fitted regression models obtained from the step 2 of this process 500 to $x^{T_k}$ and $y^{T_k}$ to predict the methylation levels of CpG sites in $T_k$ for sample t under the hypothesis that sample t is from a normal. Let $n_k$ be the number of CpG sites in $T_k$. Define functions $f_k(x_1, \ldots, x_{n_k})=\Sigma_i(-1)^I \cdot (e_{i,k}-e_i)X_i$ and $f_{k,g}(X_1, \ldots, X_{n_k})=\Sigma_i(-1)I\_(e_{i,k}-e_{i,g})X_i$, where $I\_(\bullet)=I_{(-\infty,0)}$(108), that is, the indicator function for the interval $(-\infty, 0)$, $e_i$, $e_{i,k}$ and $e_{i,g}$ are estimations obtained from step 1.5 of the the process 500. It will be said the sample is from an individual with the $k^{th}$ type of abnormal phenotype if $f_k(e_{1,t}-e_1, \ldots, e_{n_k,t}-e_{n_k})>c_{4,k}$, and $f_{k,g}(e_{1,t}-e_{1,g}, \ldots, e_{n_k,t}-e_{n_k,g})>c_{5,g}$ for all $g \ne k$, where $e_{i,t}$ is the difference between the observed methylation level of the CpG site $i \in T_k$ for sample t and the predicted value by the fitted model obtained from step 2, and $g \ne k$ is any type of abnormal phenotype that is different form the $k^{th}$ type of abnormal phenotype.

Other ways of implementing the process 500 can be developed by modifying the implementation presented above. Specifically, it does not need to assume that there are only two component reference methylomes that make up the biologic methylomes, nor does it need to estimate them directly. Instead, a set of predictor methylomes can be collected that are mixtures of component reference genomes, as long as the number of the predictor methylomes is the same as the number of the reference component methylomes, and the mixture vectors of the predictor methylomes are linearly independent. For example, they can be methylomes of biologic samples with known different proportion of first and second cell type DNAs.

In process 500, the difference between observed methylation levels in certain target regions and the predicted methylation levels as the test statistic to determine if in a biologic sample the methylome has been affect by some type of tissue abnormality. To illustrate the advantage of this approach, it is assumed that the mixture vector $p_j$ for the methylome of a normal biologic sample j followed a Dirichlet's distribution with parameters $\alpha_1 = \ldots = \alpha_R$. Furthermore, for CpG site i, its methylation levels in the R reference vector $p_j$ for component methylomes are $m_{i,r} = (r-1)/(R-1)$. It can be shown that the methylation level of i in sample j then has a mean of 0.5, and a variance of $$\frac{R+1}{12(R-1)(R\alpha_1+1)}.$$

It there is a methyl-seq library in sample j with a coverage of N for CpG site i, the variance of the measured methylation level $z_{i,j}$ is $$\sigma_1^2 = \frac{1}{4N} + \frac{N-1}{N}\frac{R+1}{12(R-1)(R\alpha_1+1)}.$$

In other words, if $z_{i,j}$ is used as a test statistic to detect abnormal intestinal tissue using biologic sample, under the null hypothesis, the test statistic has a variance of $\sigma_1^2$. However, in process 500, it is first estimated the mixture vector $p_j$, then predicted $z_{i,j}$ by $\Sigma_r m_{i,r} P_{r,j}$. Note that in a methyl-seq data, each library can cover millions of CpG sites, and that the variance of the coefficients in a linear regression model is inversely proportional to sample size. Thus it is possible to obtain highly accurate estimation of the mixture vector $p_j$, even if it is taken into account that adjacent CpG sites tend to have correlated methylation levels. Assuming an accurate estimate of $\Sigma_r m_{i,r} p_{r,j}$ can be obtained, that is, the error of the estimation can be ignored, the variance of the difference $z_{i,j} - \Sigma_r m_{i,r} p_{r,j}$ between the observed methylation level and the prediction will be $$\frac{1}{4N} - \frac{1}{N}\frac{R+1}{12(R-1)(R\alpha_1+1)}.$$

In other words, under the null hypothesis, the test static $z_{i,j} - \Sigma_r m_{i,r} p_{r,j}$ used in process 500 has a much smaller variance than the other candidate test statistic $z_{i,j}$. This in turns means that the presently disclosed test will achieve a higher power at the same level of type I error.

Additional techniques for detecting, assessing, monitoring, or treating preeclampsia can include those set forth in U.S. application Ser. No. 62/832,157, which is incorporated by reference in this disclosure.

Additional techniques for detecting, assessing, monitoring, or treating CNS conditions can include those set forth in U.S. application Ser. No. 62/882,215, which is incorporated by reference in this disclosure.

Additional techniques for detecting, assessing, or monitoring fetal aneuploidy can include those set forth in U.S. application Ser. No. 62/928,156, which is incorporated by reference in this disclosure.

Additional techniques for detecting, assessing, monitoring, or treating ovarian cancer can include those set forth in U.S. application Ser. No. 63/007,218, which is incorporated by reference in this disclosure.

Additional techniques for detecting, assessing, monitoring, or treating endometriosis can include those set forth in U.S. application Ser. No. 63/007,204, which is incorporated by reference in this disclosure.

Additional techniques for detecting, assessing, monitoring, or treating necrotizing enterocolitis can include those set forth in U.S. application Ser. No. 63/007,208, which is incorporated by reference in this disclosure.

Figure 6:
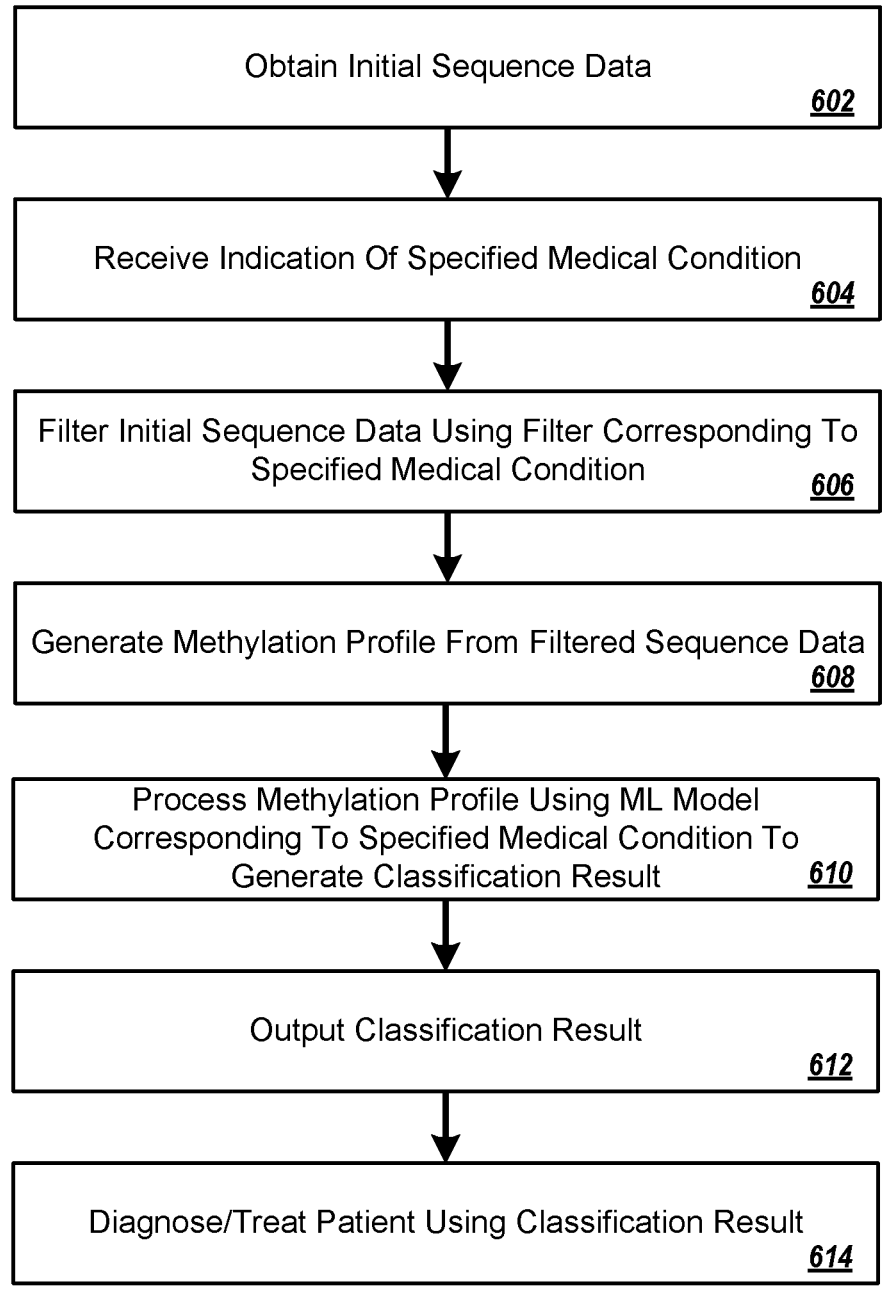
FIG. 6 is a flowchart of an example process for processing sequence data for nucleic acids from a biological sample to determine a methylation profile of the sample and classify a person with respect to the specified medical condition.

FIG. 6 is a flowchart of an example process 600 for processing sequence data for nucleic acids from a biological sample to determine a methylation profile of the sample and classify a person with respect to a specified medical condition. The process 600 can be carried out in whole or in part by systems of one or more computers, e.g., systems 102, 110, or 120. It should also be appreciated that aspects of the process 600 may incorporate operations from process 500 of FIG. 5 as previously described.

The process 600 can include obtaining an initial set of sequence data (602). The initial sequence data describes sequences of nucleic acids from a biologic sample of a person or other mammal. In some examples, the nucleic acids characterized in the initial sequence data include cell-free DNA. The initial sequence data may include cell-free DNA from various tissues of the person, including tissues affected by a specified medical condition and tissues that are not affected, or are substantially less affected, by the specified medical condition. DNA fragments corresponding to the affected tissues may be deemed target DNA (e.g., DNA from the intestinal region when assessing necrotizing enterocolitis), while fragments corresponding to the other tissues may be deemed background or non-targeted DNA. The system receives an indication of the specified medical condition that is to be screened, e.g., based on user input provided into a computing terminal (604). The initial sequence data can be filtered using a selected filter corresponding to the specified medical condition (606). In some implementations, the filtering is operable to increase a fraction of sequences for target DNA relative to other DNA. In some implementations, the filtering includes selecting target nucleic acids from an initial set of nucleic acids based a methylation characteristic (e.g., methylation status), a copy number characteristic of the target nucleic acids, or both, and enriching the target nucleic acids, e.g., to increase a fraction of the target nucleic acids after filtering relative to their fraction in a pre-filtered set. A methylation profile can be generated from the filtered sequence data (608), and the methylation profile processed with an appropriate machine-learning model corresponding to the specified medical condition to generate a classification result (610). In some implementations, the machine-learning model is a model corresponding to those described with respect to the process 500 of FIG. 5. The classification result can indicate that the person's condition is normal and does not exhibit the disease or specified medical condition, or the classification result can indicate that the person's condition is abnormal and does exhibit the disease or specified medical condition. The classification result can be provided as output by the system in a number of ways (612). For example, the classification result may be presented to one or more users on an electronic display, presented audibly through an intelligent assistant device including a speaker, transmitted to a user as a message via one or more channels (e.g., email, text messages, private social media messages). In some implementations, the system may alert the patient, his or her healthcare provider, or both, of the classification result. The healthcare provider can use the classification result to diagnose the patient with the specified medical condition, inform a determination of how and whether to treat the patient for the specified medical condition, and/or inform a determination of whether further testing or assessment should be performed to screen the patient for the specified medical condition or another medical condition (614).

The subject can be treated by administration of different therapeutic agents dependent on the specified medical condition. Where the specified medical condition is cancer (e.g., ovarian cancer), the therapeutic agent can be at least one of an immunotherapy or a chemotherapy. Where the specified medical condition is endometriosis, the therapeutic agent can be a hormone therapy. Where the specified medical condition is necrotizing enterocolitis, the therapeutic agent can be an antibiotic therapy (e.g., ampicillin, gentamycin, vancomycin, cefepime, or metronidazole). Where the specified medical condition is preeclampsia, the therapeutic agent can be an anti-hypertensive medication. The dosing level, dosing interval, or both of the therapeutic agent can be set based on the methylation level of a respective set of genomic loci associated with the specified medical condition.

This document also provides methods for treating a subject having a specified medical condition. For example, a mammal (e.g., a human female) that was identified as having endometriosis as described herein (or identified as being at risk of developing endometriosis as described herein) can be administered one or more hormone therapies, one or more pain medications, or a combination thereof to treat endometriosis. Examples of hormone therapies that can be used as described herein include, without limitation, gonadotropin-releasing hormone therapies (e.g., elagolix), estrogen therapies, progestin therapies, estrogen and progestin combination therapies, progesterone therapies, progesterone and progestin combination therapies, danazol therapies, and gestrinone therapies. Examples of pain medications that can be used as described herein include, without limitation, nonsteroidal anti-inflammatory drugs. In some cases, a mammal (e.g., a human female) that was identified as having endometriosis as described herein (or identified as being at risk of developing endometriosis as described herein) can be treated using a surgical procedure to treat endometriosis. Examples of surgical procedures that can be used as described herein include, without limitation, laparoscopic surgeries to remove one or more endometriosis patches, laparotomy surgeries to remove one or more endometriosis patches, and surgeries to sever pelvic nerves (e.g., presacral neurectomy or laparoscopic uterine nerve ablation surgeries).

In some cases, the information provided by the methods described herein can be used by a clinician or physician in determining the most effective course of treatment (e.g., preventative or therapeutic) for the subject. A course of treatment refers to the measures taken for a patient after the prognosis or the assessment of increased risk for development of endometriosis is made. For example, when a subject is identified to have an increased risk of developing endometriosis, the physician can determine whether frequent monitoring of DNA methylation changes can be performed as a prophylactic measure. Also, when a subject is diagnosed with endometriosis (e.g., based on the presence of a DNA methylation pattern in a sample from a subject), it can be advantageous to follow such detection with a therapeutic treatment.

In some cases, this document provides methods for assessing the efficacy of a therapeutic or prophylactic therapy for treating endometriosis in a subject, comprising determining the methylation status of one or more genomic loci present in a sample obtained from a subject prior to the therapy and determining methylation status of the one or more genomic loci present in a sample obtained from the subject at one or more time points during the therapeutic or prophylactic therapy, wherein the therapy is efficacious for treating endometriosis in a subject when there is a change in the presence and/or level of methylation of the one or more genomic loci in the second or subsequent samples, relative to the first sample. In certain embodiments, the first sample is obtained after therapeutic treatment has begun.

In certain embodiments, the methods for monitoring the response in a subject to prophylactic or therapeutic treatment of endometriosis or other medical conditions can include measuring the methylation status and/or level of one or more genomic loci in a sample of a subject at a first time-point, administering a therapeutic agent, re-measuring the methylation status and/or level of the one or more genomic loci at a second time-point, comparing the results of the first and second measurements and optionally modifying the treatment regimen based on the comparison. In certain embodiments, the first timepoint can be prior to an administration of the therapeutic agent, and the second time-point can be after said administration of the therapeutic agent. In certain embodiments, the first time-point can be prior to the administration of the therapeutic agent to the subject for the first time. In certain embodiments, the dose (defined as the quantity of therapeutic agent administered at any one administration) can be increased or decreased in response to the comparison. In certain embodiments, the dosing interval (defined as the time between successive administrations) can be increased or decreased in response to the comparison, including total discontinuation of treatment. In addition, the methods described herein can be used to determine the efficacy of the therapeutic treatment, wherein a change in the methylation status of certain genomic loci present in a sample of a subject can indicate that the therapeutic treatment regimen can be altered, reduced, and/or stopped.

Figure 7:
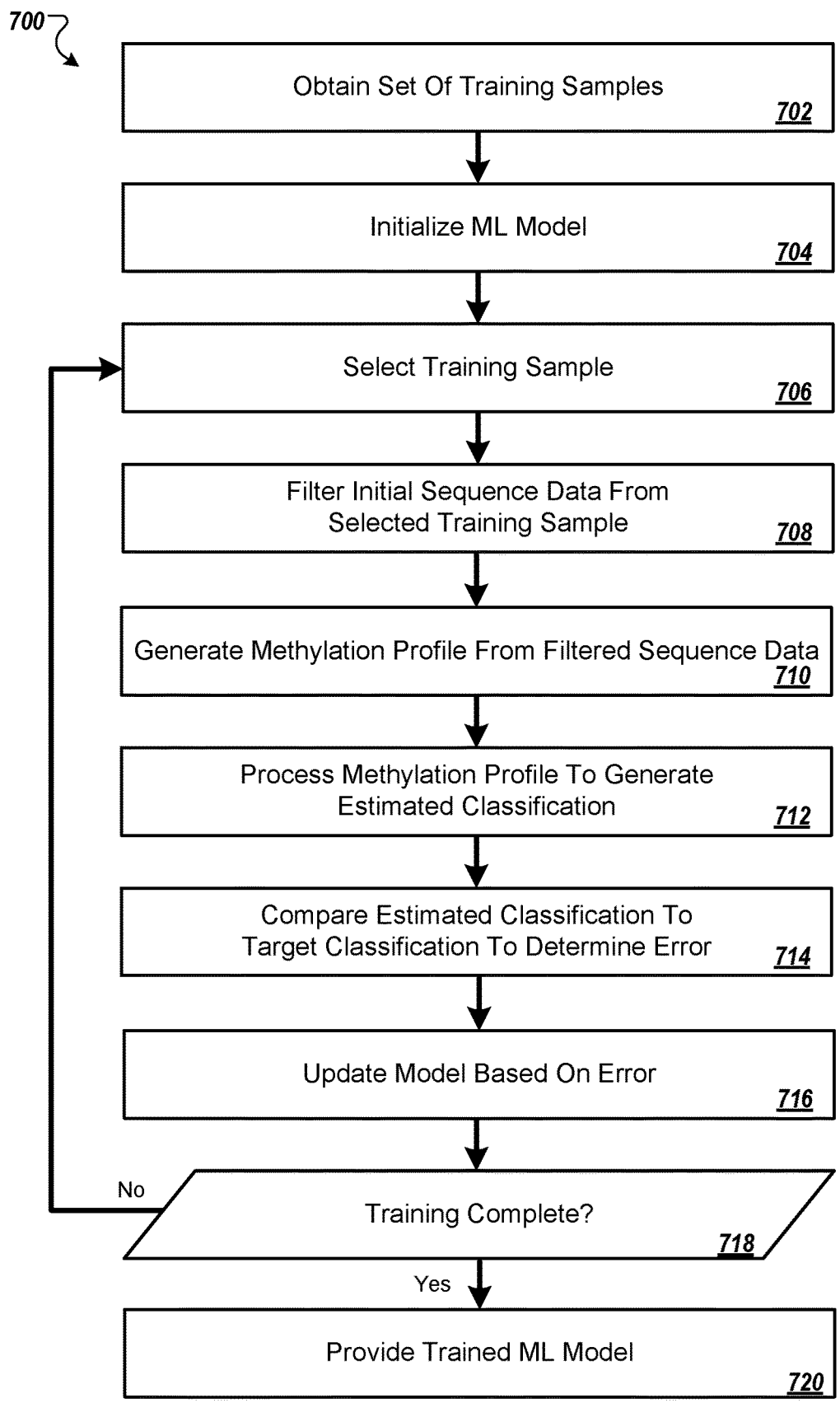
FIG. 7 is a flowchart of an example process for training a machine-learning model to generate, from a methylation profile of a patient, a classification result indicating whether a specified medical condition of the patient is or is not normal.

FIG. 7 is a flowchart of an example process 700 for training a machine-learning model to generate, from a methylation profile of a patient, a classification result indicating whether a specified medical condition of the patient is or is not normal. The system can be performed by a system of one or more computers, e.g., system 110 from the environment of FIG. 1. While process 700 relates to the training of certain types of models (e.g., feedforward neural networks) using a supervised learning technique, further description of training techniques is disclosed with respect to FIG. 5. The system obtains a set of training samples (702). Each training sample can include (i) a set of filtered or unfiltered sequence data describing sequences of nucleic acids from a biological sample of a person and (ii) a label indicating whether or not the patient exhibits a specified medical condition. The label can serve as a target output for the model 146 when evaluated on a methylation profile derived from the sequence data in the training sample. The machine-learning model is initialized (704). For example, the weights or other parameters of the model may be set to default or randomized values. An initial training sample is then selected (706), and the sequences from the selected training sample can be filtered to increase a fraction of sequences for target nucleic acids in the sequence (708). The system determines a methylation profile from the filtered sequence data (710), processes the methylation profile to generate an estimated classification (712), compares the estimated classification to the labeled/target classification to determine an error in the classification result (714), and then the error can be back-propagated through the model to update the model based on the error (e.g., using gradient descent) (716). The system checks if the training process is complete (718), e.g., by checking whether a training termination condition is satisfied. For example, training may terminate once all training samples have been consumed. The trained model can then be provided for use, e.g., by storing the model in association with a package for the corresponding medical condition (720).

Figure 8:
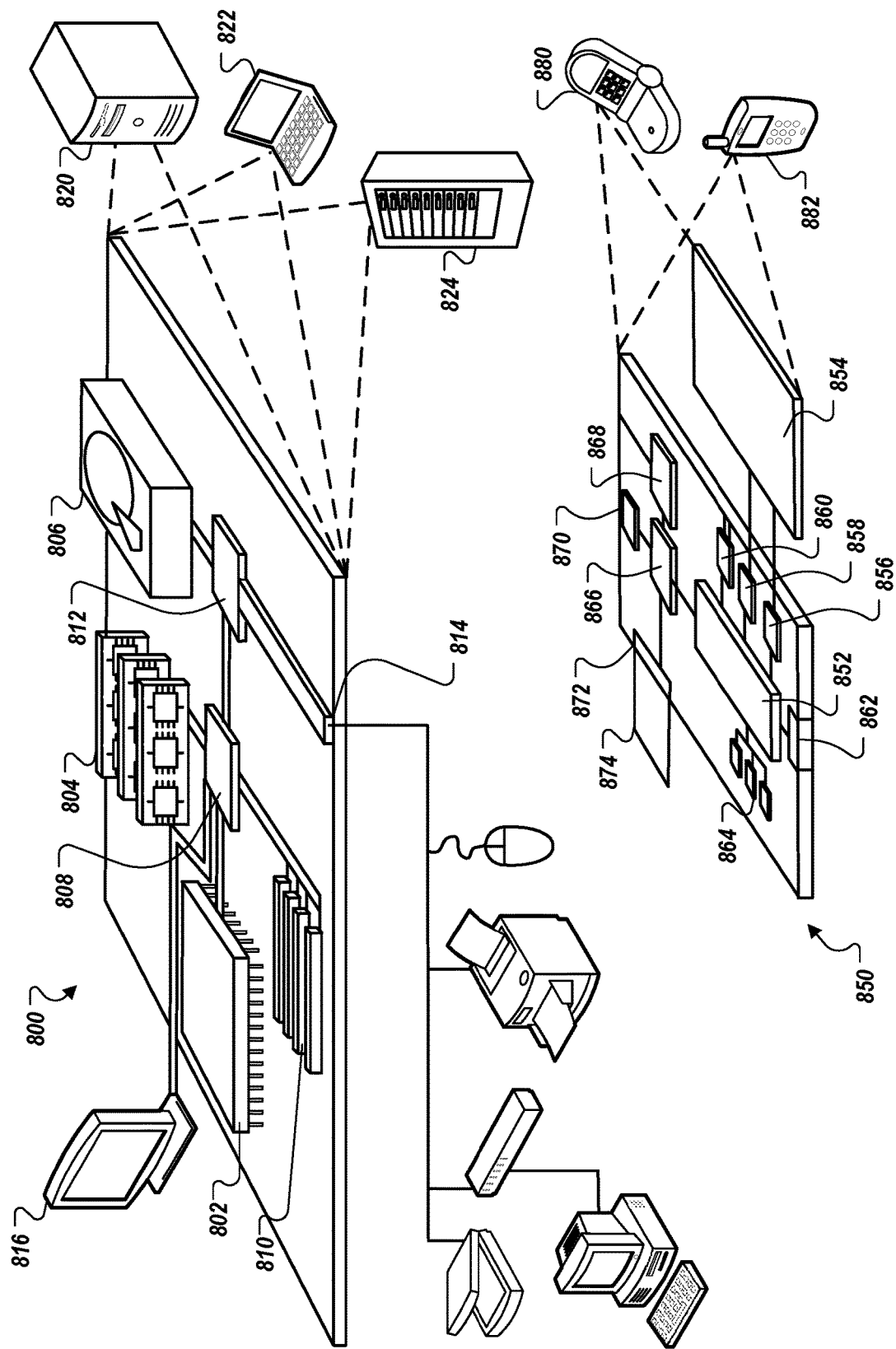
FIG. 8 depicts a block diagram of computing devices that can be used in some embodiments to implement aspects of the techniques disclosed herein.

FIG. 8 shows an example of a computing device 800 and a mobile computing device 850 that can be used in some embodiments to implement the techniques described herein. The computing device 800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. The computer program product may also contain instructions that, when executed, perform one or more methods, such as those described above. The computer program product can also be tangibly embodied in a computer- or machine-readable medium, such as the memory 804, the storage device 806, or memory on the processor 802.

The high-speed interface 808 manages bandwidth-intensive operations for the computing device 800, while the low-speed interface 812 manages lower bandwidth-intensive operations. Such allocation of functions is exemplary only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provided as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. The computer program product contains instructions that, when executed, perform one or more methods, such as those described above. The computer program product can be a computer- or machine-readable medium, such as the memory 864, the expansion memory 874, or memory on the processor 852. In some implementations, the computer program product can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth, WiFi, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Although various implementations have been described in detail above, other modifications are possible. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A method, comprising:
    obtaining initial sequence data that describes sequences of
        an initial set of nucleic acids from a biological sample of a person, the initial set of nucleic acids including nucleic acids originating from a plurality of different tissues of the person;

filtering the initial sequence data to identify a first subset of nucleic acids whose sequences correspond to sequences in a first set of genomic regions and a second subset of nucleic acids whose sequences correspond to sequences in a second set of genomic regions;

determining an observed methylation profile for the first subset of nucleic acids of the person and an observed methylation profile for the second subset of nucleic acids of the person;

determining a predicted methylation profile for the second subset of nucleic acids of the person based on the observed methylation profile for the first subset of nucleic acids of the person;

determining a likelihood that the person has a specified medical condition, including (i) determining a difference between the predicted methylation profile for the second subset of nucleic acids of the person and the observed methylation profile for the second subset of nucleic acids of the person and (ii) determining whether the difference matches a predefined pattern of deviation for the specified medical condition; and initiating a treatment of the person for the specified medical condition based on the determined likelihood that the person has the specified medical condition, the treatment including administering a therapeutic agent to the person at a dosage level or a dosage interval that is set based on a methylation level of a set of genomic loci associated with the specified medical condition, wherein (i) the specified medical condition is a cancer and the therapeutic agent comprises at least one of an immunotherapy or a chemotherapy, (ii) the specified medical condition is endometriosis and the therapeutic agent is a hormone therapy, (iii) the specified medical condition is necrotizing enterocolitis and the therapeutic agent is an antibiotic therapy, or (iv) the specified medical condition is preeclampsia and the therapeutic agent is an anti-hypertensive medication.

2. The method of claim 1, wherein filtering the initial sequence data to identify the first subset of nucleic acids comprises:

comparing nucleic acid sequences from the initial set of nucleic acids to the sequences in the first set of genomic regions;

discarding nucleic acid sequences from the initial sequence data that are not determined to match the sequences in the first set of genomic regions; and retaining nucleic acid sequences from the initial sequence data that are determined to match the sequences in the first set of genomic regions.

3. The method of claim 2, wherein at least a first subset of the first set of genomic regions are defined based on the regions in the first subset exhibiting at least a minimum level of stability with respect to at least one of the methylation characteristic or the copy number characteristic in a population of individuals.

4. The method of claim 3, wherein the second set of genomic regions are defined based on the regions in the second set exhibiting at least a minimum difference with respect to the methylation characteristic or the copy number characteristic between individuals who have the specified medical condition and individuals who do not have the specified medical condition.

5. The method of claim 1, wherein the biological sample comprises plasma, and the initial set of nucleic acids comprises cell-free DNA in the plasma.

6. The method of claim 1, comprising:

identifying a set of reference component methylomes in the initial set of nucleic acids and a filtered subset of nucleic acids;

determining a proportion of the reference component methylomes at a reference set of CpG sites in the initial set or the filtered subset of nucleic acids;

generating predictions of methylation levels at a target set of CpG sites in the initial set or the filtered subset of nucleic acids;

comparing the predictions of methylation levels at the target set of CpG sites to observed methylation levels; and determining whether the person likely has or does not have the specified medical condition based on the comparison.

7. The method of claim 1, wherein the biological sample comprises a stool sample or cerebrospinal fluid.

8. The method of claim 1, further comprising:

determining a copy number profile for a filtered subset of nucleic acids from the biological sample; and processing the copy number profile a methylation profile for the filtered subset of nucleic acids to determine the likelihood that the person has the specified medical condition.

9. The method of claim 1, wherein the initial set of nucleic acids were treated to facilitate detection of methylated sites before sequencing.

10. The method of claim 1, wherein the observed methylation profile for the first or second subsets of sequences indicates, for each of a plurality of genomic loci, a methylation level of the locus.

11. The method of claim 1, wherein the genomic loci is a CpG site, CpG island, differentially methylated region (DMR), promoter region, enhancer region, or CpG island shore.

12. The method of claim 1, wherein determining the likelihood that the person has the specified medical condition comprises determining a probability that the person has the specified medical condition.

13. The method of claim 1, wherein determining the likelihood that the person has the specified medical condition comprises generating a binary indication that the person either likely has the specified medical condition or likely does not have the specified medical condition.

14. The method of claim 1, comprising providing data representing the observed methylation profile for the second subset of nucleic acids as input to a machine-learning model.

15. The method of claim 14, wherein the machine-learning model comprises at least one of a classifier, an artificial neural network, a support vector machine, a decision tree, or a regression model.

16. The method of claim 14, wherein the machine-learning model is used to derive the predicted methylation profile for the second subset of nucleic acids is based on the observed methylation profile for the first subset of nucleic acids, wherein the machine-learning model comprises at least one of an artificial neural network, a regression tree, or a regression model.

17. The method of claim 1, wherein correlating the difference between the predicted methylation profile for the second subset of nucleic acids and the observed methylation profile for the second subset of nucleic acids with the likelihood that the person has the specified medical condition comprises comparing the difference to a minimum difference criterion.

18. The method of claim 1, wherein the predefined pattern of deviation differs for different specified medical conditions.

19. The method of claim 1, wherein administering the therapeutic agent to the person at the dosage level or the dosage interval that is set based on the methylation level of the set of genomic loci associated with the specified medical condition comprises:
administering the therapeutic agent to the person at a first dosage level or a first dosage interval;
monitoring a change in the methylation level of the set of genomic loci associated with the specified medical condition after administration of the therapeutic agent at the first dosage level or the first dosage interval; and
adjusting the administration of the therapeutic agent from the first dosage level or the first dosage interval to a second dosage level or a second dosage interval based on the change in the methylation level of the set of genomic loci associated with the specified medical condition.

20. The method of claim 1, wherein the dosage level is set based on the methylation level of the set of genomic loci associated with the specified medical condition.

21. The method of claim 1, wherein the specified medical condition is the cancer.

22. The method of claim 21, wherein the cancer is ovarian cancer.

23. The method of claim 1, wherein the specified medical condition is endometriosis.

24. The method of claim 1, wherein the specified medical condition is necrotizing enterocolitis.

25. The method of claim 1, wherein the specified medical condition is preeclampsia.

26. A computing system, comprising:
one or more processors; and
one or more non-transitory computer-readable media having instructions stored thereon that, when executed by the one or more processors, cause the one or more processors to perform operations comprising:
obtaining initial sequence data that describes sequences of an initial set of nucleic acids from a biological sample of a person, the initial set of nucleic acids including nucleic acids originating from a plurality of different tissues of the person;
filtering the initial sequence data to identify a first subset of nucleic acids whose sequences correspond to sequences in a first set of genomic regions and a second subset of nucleic acids whose sequences correspond to sequences in a second set of genomic regions;
determining an observed methylation profile for the first subset of nucleic acids of the person and an observed methylation profile for the second subset of nucleic acids of the person;
determining a predicted methylation profile for the second subset of nucleic acids of the person based on the observed methylation profile for the first subset of nucleic acids of the person;
determining a likelihood that the person has a specified medical condition, including (i) determining a difference between the predicted methylation profile for the second subset of nucleic acids of the person and the observed methylation profile for the second subset of nucleic acids of the person and (ii) determining whether the difference matches a predefined pattern of deviation for the specified medical condition
wherein a treatment of the person for the specified medical condition is initiated based on the determined likelihood that the person has the specified medical condition, the treatment including administering a therapeutic agent to the person at a dosage level or a dosage interval that is set based on a methylation level of a set of genomic loci associated with the specified medical condition,
wherein (i) the specified medical condition is a cancer and the therapeutic agent comprises at least one of an immunotherapy or a chemotherapy, (ii) the specified medical condition is endometriosis and the therapeutic agent is a hormone therapy, (iii) the specified medical condition is necrotizing enterocolitis and the therapeutic agent is an antibiotic therapy, or (iv) the specified medical condition is preeclampsia and the therapeutic agent is an anti-hypertensive medication.

27. One or more non-transitory computer-readable media having instructions stored thereon that, when executed by one or more processors, cause performance of operations comprising:
obtaining initial sequence data that describes sequences of an initial set of nucleic acids from a biological sample of a person, the initial set of nucleic acids including nucleic acids originating from a plurality of different tissues of the person;
filtering the initial sequence data to identify a first subset of nucleic acids whose sequences correspond to sequences in a first set of genomic regions and a second subset of nucleic acids whose sequences correspond to sequences in a second set of genomic regions;
determining an observed methylation profile for the first subset of nucleic acids of the person and an observed methylation profile for the second subset of nucleic acids of the person;
determining a predicted methylation profile for the second subset of nucleic acids of the person based on the observed methylation profile for the first subset of nucleic acids of the person;
determining a likelihood that the person has a specified medical condition, including (i) determining a difference between the predicted methylation profile for the second subset of nucleic acids of the person and the observed methylation profile for the second subset of nucleic acids of the person and (ii) determining whether the difference matches a predefined pattern of deviation for the specified medical condition;
initiating a treatment of the person for the specified medical condition based on the determined likelihood that the person has the specified medical condition, the treatment including administering a therapeutic agent to the person at a dosage level or a dosage interval that is set based on a methylation level of a set of genomic loci associated with the specified medical condition,
wherein (i) the specified medical condition is a cancer and the therapeutic agent comprises at least one of an immunotherapy or a chemotherapy, (ii) the specified medical condition is endometriosis and the therapeutic agent is a hormone therapy, (iii) the specified medical condition is necrotizing enterocolitis and the therapeutic agent is an antibiotic therapy, or (iv) the specified medical condition is preeclampsia and the therapeutic agent is an anti-hypertensive medication.

28. A method, comprising:
obtaining initial sequence data that describes sequences of an initial set of nucleic acids from a biological sample of a person, the initial set of nucleic acids including nucleic acids originating from a plurality of different tissues of the person;
filtering the initial sequence data to identify a first subset of sequences from the initial sequence data that correspond to a first pre-defined set of genomic regions;
filtering the initial sequence data to identify a second subset of sequences from the initial sequence data that correspond to a second pre-defined set of genomic regions;
processing data that includes an observed methylation profile of the first subset of sequences to generate a predicted methylation profile of the second subset of sequences;
determining a difference between an observed methylation profile of the second subset of sequences and the predicted methylation profile of the second subset of sequences;
determining whether the difference between the observed methylation profile of the second subset of sequences and the predicted methylation profile of the second subset of sequences matches a predefined pattern of deviation for a specified medical condition, wherein the person is deemed to have the specified medical condition if the difference between the observed methylation profile of the second subset of sequences and the predicted methylation profile of the second subset of sequences matches the predefined pattern of deviation for the specified medical condition; and
initiating a treatment of the person for the specified medical condition based on the determined likelihood that the person has the specified medical condition, the treatment including administering a therapeutic agent to the person at a dosage level or a dosage interval that is set based on a methylation level of a set of genomic loci associated with the specified medical condition,
wherein (i) the specified medical condition is a cancer and the therapeutic agent comprises at least one of an immunotherapy or a chemotherapy, (ii) the specified medical condition is endometriosis and the therapeutic agent is a hormone therapy, (iii) the specified medical condition is necrotizing enterocolitis and the therapeutic agent is an antibiotic therapy, or (iv) the specified medical condition is preeclampsia and the therapeutic agent is an anti-hypertensive medication.

29. The method of claim 28, wherein:
the first pre-defined set of genomic regions are regions that exhibit at least a minimum level of stability with respect to at least one of a methylation characteristic or a copy number characteristic in a population of individuals; and
the second pre-defined set of genomic regions are regions that exhibit at least a minimum difference with respect to at least one of the methylation characteristic or the copy number characteristic between a first sub-population of individuals who have the specified medical condition and a second sub-population of individuals who do not have the specified medical condition.

30. The method of claim 28, wherein the first pre-defined set of genomic regions is a first reference set of genomic regions, and the second pre-defined set of genomic regions is a first target set of genomic regions; the method further comprising:
selecting the first reference set of genomic regions as the first pre-defined set of genomic regions from a database that includes a plurality of reference sets of genomic regions, wherein different ones of the plurality of reference sets of genomic regions correspond to different medical conditions; and
selecting the first target set of genomic regions as the second pre-defined set of genomic regions from the database, wherein the database further includes a plurality of target sets of genomic regions, wherein different ones of the plurality of target sets of genomic regions correspond to different medical conditions.

31. One or more non-transitory computer-readable media having instructions stored thereon that, when executed by one or more processors, cause performance of operations comprising:
obtaining initial sequence data that describes sequences of an initial set of nucleic acids from a biological sample of a person, the initial set of nucleic acids including nucleic acids originating from a plurality of different tissues of the person;
filtering the initial sequence data to identify a first subset of sequences from the initial sequence data that correspond to a first pre-defined set of genomic regions;
filtering the initial sequence data to identify a second subset of sequences from the initial sequence data that correspond to a second pre-defined set of genomic regions;
processing data that includes an observed methylation profile of the first subset of sequences to generate a predicted methylation profile of the second subset of sequences;
determining a difference between an observed methylation profile of the second subset of sequences and the predicted methylation profile of the second subset of sequences;
determining whether the difference between the observed methylation profile of the second subset of sequences and the predicted methylation profile of the second subset of sequences matches a predefined pattern of deviation for a specified medical condition, wherein the person is deemed to have the specified medical condition if the difference between the observed methylation profile of the second subset of sequences and the predicted methylation profile of the second subset of sequences matches the predefined pattern of deviation for the specified medical condition;
wherein a treatment of the person for the specified medical condition is initiated based on the determined likelihood that the person has the specified medical condition, the treatment including administering a therapeutic agent to the person at a dosage level or a dosage interval that is set based on a methylation level of a set of genomic loci associated with the specified medical condition,
wherein (i) the specified medical condition is a cancer and the therapeutic agent comprises at least one of an immunotherapy or a chemotherapy, (ii) the specified medical condition is endometriosis and the therapeutic agent is a hormone therapy, (iii) the specified medical condition is necrotizing enterocolitis and the therapeutic agent is an antibiotic therapy, or (iv) the specified medical condition is preeclampsia and the therapeutic agent is an anti-hypertensive medication.

* * * * *

UNITED STATES PATENT AND TRADEMARK OFFICE
CERTIFICATE OF CORRECTION

| | | |
|---|---|---|
| PATENT NO. | : 12,009,061 B2 | Page 1 of 1 |
| APPLICATION NO. | : 16/846238 | |
| DATED | : June 11, 2024 | |
| INVENTOR(S) | : Peters et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 544 days.

Signed and Sealed this
Twelfth Day of November, 2024

Katherine Kelly Vidal
*Director of the United States Patent and Trademark Office*